US010321867B2

(12) United States Patent
Mabary et al.

(10) Patent No.: US 10,321,867 B2
(45) Date of Patent: Jun. 18, 2019

(54) METHOD OF DETECTING AND MEASURING THE CONDITION OF INTRALUMINAL ESOPHAGEAL MUCOSA

(71) Applicants: Jerry E. Mabary, Littleton, CO (US); Michael F. Vaezi, Brentwood, TN (US); Thomas D. Stuebe, Littleton, CO (US)

(72) Inventors: Jerry E. Mabary, Littleton, CO (US); Michael F. Vaezi, Brentwood, TN (US); Thomas D. Stuebe, Littleton, CO (US)

(73) Assignees: Diversatek Healthcare, Inc., Milwaukee, WI (US); Vanderbilt University, Nashville, TN (US)

( * ) Notice: Subject to any disclaimer, the term of this patent is extended or adjusted under 35 U.S.C. 154(b) by 0 days.

(21) Appl. No.: 15/425,530

(22) Filed: Feb. 6, 2017

(65) Prior Publication Data
US 2017/0143248 A1    May 25, 2017

Related U.S. Application Data

(62) Division of application No. 13/182,417, filed on Jul. 13, 2011, now Pat. No. 9,814,408.
(Continued)

(51) Int. Cl.
*A61B 5/00* (2006.01)
*A61B 5/053* (2006.01)
*A61B 5/03* (2006.01)

(52) U.S. Cl.
CPC ............ *A61B 5/4233* (2013.01); *A61B 5/037* (2013.01); *A61B 5/0538* (2013.01);
(Continued)

(58) Field of Classification Search
CPC .. A61B 2018/0022; A61B 2018/00875; A61B 17/12136; A61B 1/00082
(Continued)

(56) References Cited

U.S. PATENT DOCUMENTS 4,587,975 A * 5/1986 Salo ..................... A61B 5/0535
600/506
4,706,688 A * 11/1987 Don Michael ....... A61B 5/0421
600/380
(Continued)

FOREIGN PATENT DOCUMENTS

WO    2009/113064 A2    9/2009

OTHER PUBLICATIONS

European Patent Office, Extended Search Report for corresponding Application No. EP 11807487.1, dated Jan. 30, 2015, 7 pages.
(Continued)

*Primary Examiner* — May A Abouelela
(74) *Attorney, Agent, or Firm* — Quarles & Brady LLP

(57) ABSTRACT

A method of detecting and measuring the condition of intraluminal esophageal mucosa. An esophagus is intubated with a catheter including an inflatable and deflatable balloon and one or more impedance sensing electrodes on an exterior surface of the catheter. The balloon is inflated to press the impedance sensing electrode(s) into a mucosa of the interior esophageal wall. An electric current is directed through the mucosa via the impedance sensing electrode(s) while the impedance sensing electrode(s) is/are pressed by the balloon against the mucosa and measure impedance of the mucosa.

27 Claims, 16 Drawing Sheets

Related U.S. Application Data

(60) Provisional application No. 61/447,605, filed on Feb. 28, 2011, provisional application No. 61/363,997, filed on Jul. 13, 2010.

(52) U.S. Cl.
CPC ............ *A61B 5/4211* (2013.01); *A61B 5/687* (2013.01); *A61B 5/6853* (2013.01); *A61B 5/6885* (2013.01); *A61B 5/7282* (2013.01); *A61B 2562/0209* (2013.01); *A61B 2562/046* (2013.01); *A61B 2562/168* (2013.01)

(58) Field of Classification Search
USPC ......... 600/547, 587, 593, 466, 470; 606/192
See application file for complete search history.

(56) References Cited

U.S. PATENT DOCUMENTS

| | | | | |
|---|---|---|---|---|
| 4,809,710 A * | 3/1989 | Williamson | ............ | A61B 5/036 600/561 |
| 4,840,182 A * | 6/1989 | Carlson | ................ | A61B 5/0538 600/505 |
| 4,852,580 A * | 8/1989 | Wood | ...................... | A61B 5/026 600/506 |
| 4,981,470 A * | 1/1991 | Bombeck, IV | ........ | A61B 5/037 128/205.23 |
| 5,024,228 A * | 6/1991 | Goldstone | ............ | A61B 5/0421 600/380 |
| 5,056,532 A | 10/1991 | Hull et al. | | |
| 5,087,244 A * | 2/1992 | Wolinsky | ............... | A61M 25/10 604/103.01 |
| 5,109,870 A * | 5/1992 | Silny | ...................... | A61B 5/037 600/373 |
| 5,479,935 A * | 1/1996 | Essen-Moller | ........ | A61B 5/037 600/547 |
| 5,551,439 A * | 9/1996 | Hickey | ................. | A61B 5/0215 600/486 |
| 5,553,611 A * | 9/1996 | Budd | .................... | A61B 5/0422 600/374 |
| 5,617,876 A * | 4/1997 | van Duyl | .............. | A61B 5/0422 600/373 |
| 5,687,737 A * | 11/1997 | Branham | .............. | A61B 5/0422 600/509 |
| 5,769,846 A * | 6/1998 | Edwards | ............... | A61B 18/148 602/22 |
| 5,782,774 A | 7/1998 | Shmulewitz | | |
| 5,791,349 A | 8/1998 | Shmulewitz | | |
| 5,833,625 A * | 11/1998 | Essen-Moller | ........ | A61B 5/037 600/547 |
| 5,860,974 A * | 1/1999 | Abele | ...................... | A61B 8/12 600/374 |
| 6,006,755 A | 12/1999 | Edwards | | |
| 6,095,987 A * | 8/2000 | Shmulewitz | .......... | A61B 5/0535 600/506 |
| 6,104,941 A * | 8/2000 | Huey | ................... | A61B 5/0448 600/338 |
| 6,292,689 B1 * | 9/2001 | Wallace | .................. | A61B 5/029 600/547 |
| 6,315,733 B1 * | 11/2001 | Zimmon | ............ | A61B 5/02152 600/481 |
| 6,358,245 B1 * | 3/2002 | Edwards | ............... | A61B 18/12 128/922 |
| 6,666,828 B2 * | 12/2003 | Greco | ..................... | A61B 5/205 600/561 |
| 6,728,562 B1 * | 4/2004 | Budd | .................... | A61B 5/04085 600/374 |
| 6,882,879 B2 | 4/2005 | Rock | | |
| 6,965,795 B2 | 11/2005 | Rock | | |
| 6,974,456 B2 | 12/2005 | Edwards et al. | | |
| 7,184,812 B2 * | 2/2007 | Sinderby | ............ | A61B 5/04884 600/380 |
| 7,236,820 B2 * | 6/2007 | Mabary | .................. | A61B 5/037 600/547 |
| 7,454,244 B2 * | 11/2008 | Kassab | .................. | A61B 5/053 600/547 |
| 7,476,204 B2 * | 1/2009 | Parks | ..................... | A61B 5/037 600/372 |
| 7,555,329 B2 * | 6/2009 | Gross | .................... | A61B 6/481 424/9.1 |
| 7,585,296 B2 * | 9/2009 | Edwards | ............ | A61B 18/1477 606/41 |
| 7,654,997 B2 * | 2/2010 | Makower | ............... | A61B 17/24 604/509 |
| 7,736,320 B2 * | 6/2010 | Tsukashima | ........... | A61B 5/083 204/433 |
| 7,818,155 B2 * | 10/2010 | Stuebe | ................... | A61B 5/053 703/11 |
| 7,856,277 B1 * | 12/2010 | Thacker | ................ | A61N 1/0558 607/117 |
| 8,103,338 B2 * | 1/2012 | Harlev | ................. | A61B 5/0536 600/547 |
| 8,106,905 B2 * | 1/2012 | Markowitz | ........... | A61B 5/0422 345/419 |
| 8,224,422 B2 * | 7/2012 | Mottola | ............... | A61B 1/0008 600/424 |
| 8,306,290 B2 * | 11/2012 | Parks | ..................... | A61B 5/037 382/128 |
| 8,371,303 B2 * | 2/2013 | Schaner | ............... | A61M 16/04 128/200.24 |
| 8,386,010 B2 * | 2/2013 | Beetel | ..................... | A61B 5/053 324/447 |
| 8,521,249 B2 * | 8/2013 | O'Dea | .................. | A61B 5/0538 600/373 |
| 8,551,096 B2 * | 10/2013 | Perry | .................. | A61B 18/1492 604/382 |
| 8,568,336 B2 * | 10/2013 | Gewolb | .................. | A61B 5/11 600/300 |
| 2004/0171942 A1 * | 9/2004 | Ackerman | ............. | A61B 5/037 600/486 |
| 2004/0215296 A1 * | 10/2004 | Ganz | ..................... | A61B 5/0538 607/99 |
| 2004/0230110 A1 | 11/2004 | Sinderby et al. | | |
| 2004/0254495 A1 * | 12/2004 | Mabary | .................. | A61B 5/037 600/547 |
| 2005/0065450 A1 * | 3/2005 | Stuebe | ................... | A61B 5/037 600/547 |
| 2005/0080832 A1 * | 4/2005 | Stuebe | ................... | A61B 5/053 708/400 |
| 2006/0004304 A1 * | 1/2006 | Parks | ..................... | A61B 5/037 600/593 |
| 2006/0015162 A1 * | 1/2006 | Edward | ............ | A61B 18/1477 607/105 |
| 2006/0095032 A1 * | 5/2006 | Jackson | .......... | A61M 25/10184 606/41 |
| 2006/0116564 A1 * | 6/2006 | Mintchev | ............... | A61B 5/037 600/350 |
| 2006/0178587 A1 * | 8/2006 | Khoury | ............... | A61B 5/0535 600/509 |
| 2006/0282071 A1 * | 12/2006 | Utley | ..................... | A61B 18/12 606/41 |
| 2007/0135809 A1 * | 6/2007 | Utley | .................. | A61B 18/1492 606/41 |
| 2007/0225613 A1 * | 9/2007 | Mabary | .................. | A61B 5/037 600/547 |
| 2008/0004547 A1 * | 1/2008 | Dinsmoor | .............. | A61B 5/073 600/593 |
| 2008/0033316 A1 * | 2/2008 | Kassab | .................. | A61B 5/053 600/547 |
| 2008/0077043 A1 * | 3/2008 | Malbrain | ............... | A61B 5/036 600/547 |
| 2008/0121231 A1 * | 5/2008 | Sinderby | ............... | A61B 5/037 128/204.21 |
| 2008/0125772 A1 * | 5/2008 | Stone | .................. | A61B 18/1492 606/41 |
| 2008/0161730 A1 * | 7/2008 | McMahon | ............ | A61B 5/227 600/593 |

(56) References Cited

U.S. PATENT DOCUMENTS

| | | | |
|---|---|---|---|
| 2008/0188912 A1* | 8/2008 | Stone | A61B 18/1492 607/99 |
| 2008/0194996 A1* | 8/2008 | Kassab | A61B 5/053 600/593 |
| 2008/0306411 A1* | 12/2008 | Stuebe | A61B 5/053 600/593 |
| 2008/0319350 A1* | 12/2008 | Wallace | A61B 5/053 600/587 |
| 2009/0012512 A1* | 1/2009 | Utley | A61B 18/0218 606/21 |
| 2009/0062684 A1* | 3/2009 | Gregersen | A61B 5/02007 600/547 |
| 2009/0118637 A1* | 5/2009 | Kassab | A61B 5/053 600/547 |
| 2009/0124937 A1* | 5/2009 | Parks | A61B 5/037 600/593 |
| 2009/0131928 A1* | 5/2009 | Edwards | A61B 18/00 606/33 |
| 2009/0192405 A1* | 7/2009 | Carney | A61B 17/320758 600/547 |
| 2009/0240162 A1* | 9/2009 | Stuebe | A61B 5/037 600/547 |
| 2009/0306589 A1* | 12/2009 | Tilson | A61B 17/8816 604/103.1 |
| 2010/0004648 A1* | 1/2010 | Edwards | A61B 18/1477 606/33 |
| 2010/0113939 A1* | 5/2010 | Mashimo | A61B 5/02158 600/470 |
| 2010/0125239 A1* | 5/2010 | Perry | A61B 5/053 604/21 |
| 2010/0137738 A1* | 6/2010 | Beetel | A61B 5/053 600/547 |
| 2010/0160906 A1* | 6/2010 | Jarrard | A61B 18/1492 606/33 |
| 2010/0168743 A1* | 7/2010 | Stone | A61B 5/02007 606/42 |
| 2010/0191089 A1* | 7/2010 | Stebler | A61B 5/053 600/373 |
| 2010/0204560 A1* | 8/2010 | Salahieh | A61B 5/01 600/373 |
| 2010/0234840 A1* | 9/2010 | Jackson | A61M 25/10184 606/34 |
| 2010/0268110 A1 | 10/2010 | Beltran et al. | |
| 2010/0305479 A1* | 12/2010 | O'Dea | A61B 5/037 600/587 |
| 2011/0306897 A1* | 12/2011 | Imran | A61B 5/0538 600/547 |
| 2012/0209086 A1* | 8/2012 | Beute | A61B 5/6853 600/301 |

OTHER PUBLICATIONS

Intellectual Property Office, Examination Report Under Section 18(3) for corresponding Application No. GB1302430.2, dated Jun. 17, 2015, 6 pages.

Patent Cooperation Treaty—International Searching Authority, International Search Report and Written Opinion for corresponding Application No. PCT/US2011/043926, dated Nov. 22, 2011, 11 pages.

Radu Tutuian, M.D. and Donald O. Castell, M.D., Gastroesophageal reflux monitoring: pH and impedance, Goyal & Shaker Gi Motility online, printed Nov. 9, 2011, 12 pages, Nature Publishing Group, a division of Macmillan Publishers Limited.

John Pandolfino, MD, Feinberg School of Medicine, Northwestern University, Esophageal Monitoring Devices, US Gastroenterology Review 2007, pp. 23-26, copyright Touch Briefings 2007.

Radu Tutuian and Donald O. Castell, Rumination documented by using combined multichannel intraluminal impedance and manometry, Abstract—Clinical Gastroenterology and Hepatology, vol. 2, Issue 4, 2 pages from internet, printed Nov. 9, 2011, copyright 2004 American Gastroenterological Association, published by Elsevier Inc.

German Patent and Trademark Office, First Official Communication, Application No. 11 2011 102 344.8, dated Oct. 31, 2018, 21 pages.

* cited by examiner

METHOD OF DETECTING AND MEASURING THE CONDITION OF INTRALUMINAL ESOPHAGEAL MUCOSA

CROSS-REFERENCE TO RELATED APPLICATIONS

This application is a divisional of U.S. patent application Ser. No. 13/182,417, titled "Display System for Displaying Conditions of Esophageal Mucosa and Indications of Gastroesophageal Reflux Disease" filed Jul. 13, 2011, which claims the benefit of U.S. Provisional Patent Application No. 61/363,997, titled "Apparatus and Method for Mucosal Impedance Diagnostic Testing for Gastroesophageal Reflux Disease" filed Jul. 13, 2010, and U.S. Provisional Application No. 61/447,605, titled "Apparatus and Method for Measuring Impedance of Esophageal Mucosa" filed Feb. 28, 2011, all of which applications are hereby specifically incorporated herein by reference for all they disclose and teach.

BACKGROUND

Gastroesophageal Reflux Disease is a very common symptom serving as the basis for 22% of primary care visits. Current estimates are that 14% of Americans suffer from Gastroesophageal Reflux Disease on at least a weekly basis. The demographics of Gastroesophageal Reflux Disease have increased markedly over the past years as fueled by factors of poor diet, increasing body mass index (BMI), and sedentary lifestyle.

Under the Montreal definition, Gastroesophageal Reflux Disease is defined as "a condition which develops when the reflux of the stomach contents causes troublesome symptoms and/or complications." Esophageal damage secondary to gastroesophageal reflux can include reflux esophagitis (inflammatory damage of the esophageal lining called mucosa), and Barrett's esophagus, an abnormal change (metaplasia) in the cells of the distal portion of the esophagus wherein normal squamous epithelium lining of the esophagus is replaced by metaplastic columnar epithelium. Barrett's esophagus has a strong association with esophageal adenocarcinoma, a particularly lethal cancer. Symptoms are considered troublesome if they adversely impact a patient's well-being. Common symptoms, which can compromise the patient's well-being, include heartburn, regurgitation, and chest pain. Atypical symptoms, which can compromise a patient's well-being, include chronic cough, chronic throat clearing, hoarseness, and respiratory disorders, such as asthma and recurrent pneumonia.

Gastroesophageal reflux is characterized by bolus movements progressing retrograde from the stomach to the esophagus, which can be detected and monitored with commercially available multichannel intraluminal impedance (MU) and acid detecting probes pH inserted through the nose or mouth into the esophagus, such as MU equipment manufactured by Sandhill Scientific, Inc., of Highlands Ranch, Colo., USA. Reflux esophagitis and Barrett's esophagus can be detected by endoscopic visual observation and biopsies analyzed by electron microscopy. U.S. Pat. No. 7,818,155, issued to Stuebe et al., which is incorporated herein by reference, teaches detecting reflux and bolus transit in the esophagus with MU equipment and that such detection is enhanced by using a different (lower) impedance baseline in the signal processing for patients with diseased esophageal tissue than for more healthy patients.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

BRIEF DESCRIPTION OF THE DRAWINGS

The accompanying drawings, which are incorporated herein and form a part of the specification, illustrate some, but not the only or exclusive, example embodiments and/or features. It is intended that the embodiments and figures disclosed herein are to be considered illustrative rather than limiting.

In the drawings.

DETAILED DESCRIPTION OF EXAMPLE IMPLEMENTATIONS

Figure 1:
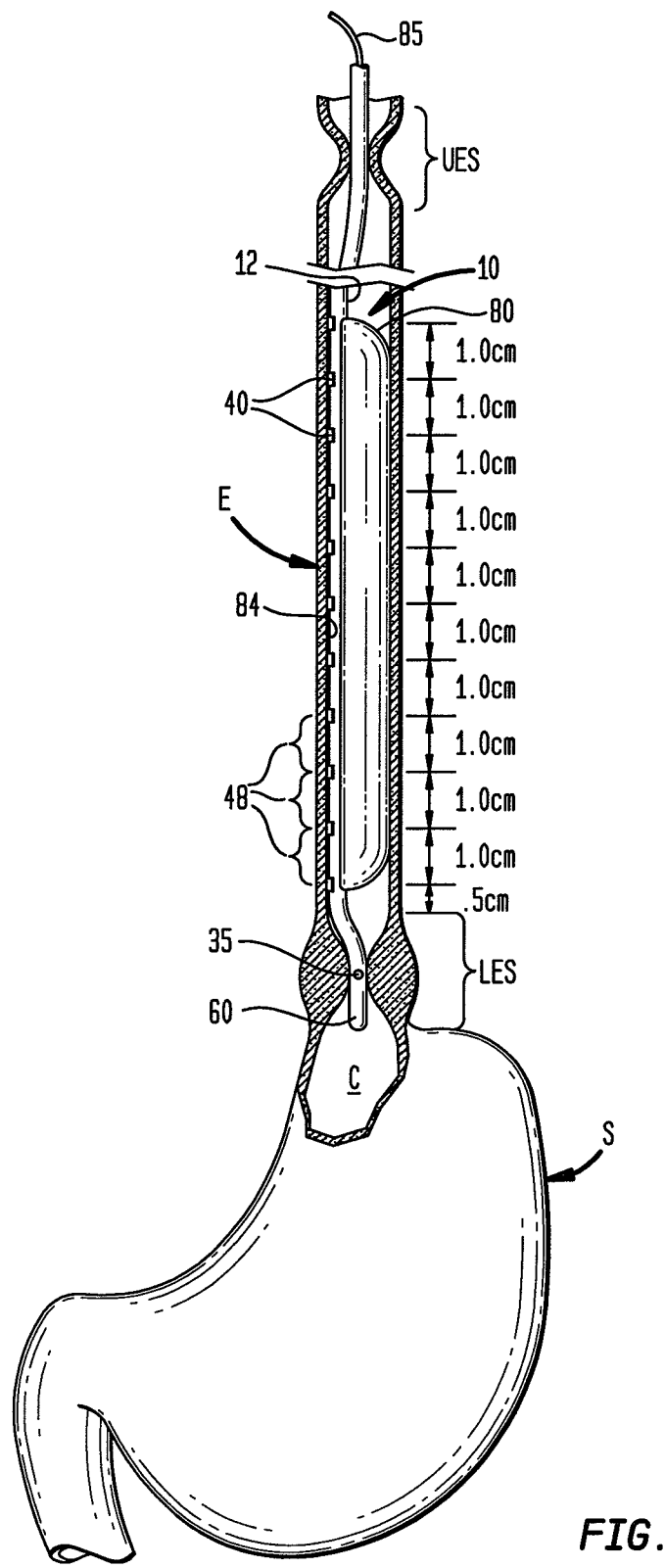
FIG. 1 is diagrammatic elevation view of an example embodiment of a multichannel intraluminal impedance catheter with a tube on which the impedance sensor electrodes are mounted and an inflatable displacing balloon or bladder also mounted on the catheter tube to push the tube and impedance sensor electrodes to one side of the esophagus into contact with the mucosal tissue on the interior wall of the esophagus.

An example embodiment of a mucosal impedance catheter 10 for measuring impedance of esophageal mucosa is illustrated diagrammatically in FIGS. 1-4 positioned in an esophagus E with an inflated balloon or bladder 80 to push the catheter tube 12 and the mucosal Impedance sensor electrodes 40 on the catheter tube 12 into direct contact with the mucosa of the interior wall 84 of the esophagus E. When the balloon or bladder 80 is expanded, for example, by inflation, the impedance sensor electrodes 40 are pressed against the mucosa on the interior wall 84 of the esophagus E, as illustrated in FIG. 1, displacing air, liquid, bolus remnants or other artifacts (not shown) that may have been between any of the electrodes 40 and the mucosa. Therefore, such pressing of the sensor electrodes 40 against the mucosa enhances likelihood of direct contact of the electrodes 40 with the mucosa, which enhances direct, accurate measurement of the impedance of the mucosa with little or no interference from air, liquid, bolus remnants, or other artifacts, that may have different impedance values than the mucosa. The catheter tube 12 is non-conductive, so it does not affect or interfere with measurements of impedance between the electrodes 40.

Measuring intraluminal impedance in the esophagus is well-known to persons skilled in the art, as taught, for example, in U.S. Pat. No. 5,109,870, issued to Silny et al., or U.S. Pat. No. 7,818,155, issued to Stuebe et al., thus does not need to be described further for purposes of this invention. Suffice it to say that impedance, which is opposition to flow of electric current, can be measured between any of the contacts or impedance sensor electrodes 40 on the catheter tube 12. While any impedance measuring instrumentation and methodology will work, a simple example is to provide a constant voltage source connected across a pair of conductive contacts, e.g., any pair of the electrodes 40, to make an electric current flow between that pair of contacts 40. The current flow can be measured by an ammeter or similar instrumentation, for example, in the processing electronics 106 shown in FIG. 5. According to Ohm's law, the magnitude of the electric current measured is proportional to the impedance of the material through which the electric current flows between the contact or sensor electrodes 40. Therefore, if the mucosa on the interior wall 84 of the esophagus E is positioned across any two of the contact or sensor electrodes 40 of the catheter 10, as illustrated in FIG. 1, the electric current measured is dependent at least in part on the impedance of the mucosa. On the other hand, if the mucosa is not positioned across two of the electrodes 40, then the current measurement will be inversely proportional to the impedance of whatever other material the current has to flow through in order to complete the electric circuit, e.g., saliva, air, bolus in the esophagus, or whatever. Therefore, a mechanism, such as the balloon 80 for pushing the catheter tube 12 and its electrodes 40 against the mucosa of the inner esophageal wall 84, is important to accurate direct impedance measurements of the mucosa. The lower the impedance of the material across the electrodes 40, the greater the current flow will be, and vice versa. It is also possible to measure the impedance of the mucosa with only one electrode on the catheter 10 if there is another electrode or contact in the electric circuit somewhere else on the patient's body (not shown) to complete an electric circuit in a manner that causes current to flow through the mucosa from or to the single electrode. However, such single electrode systems may have safety and accuracy issues that are not as easily controllable and manageable as the example multiple electrodes 40 on the catheter tube 12 as shown in FIGS. 1-4. In any event, some current control or limiting device or circuitry connected to the electrode or electrodes 40 can be used to prevent the flow of too much electric current, which could bum or otherwise injure the tissue.

Figure 3:
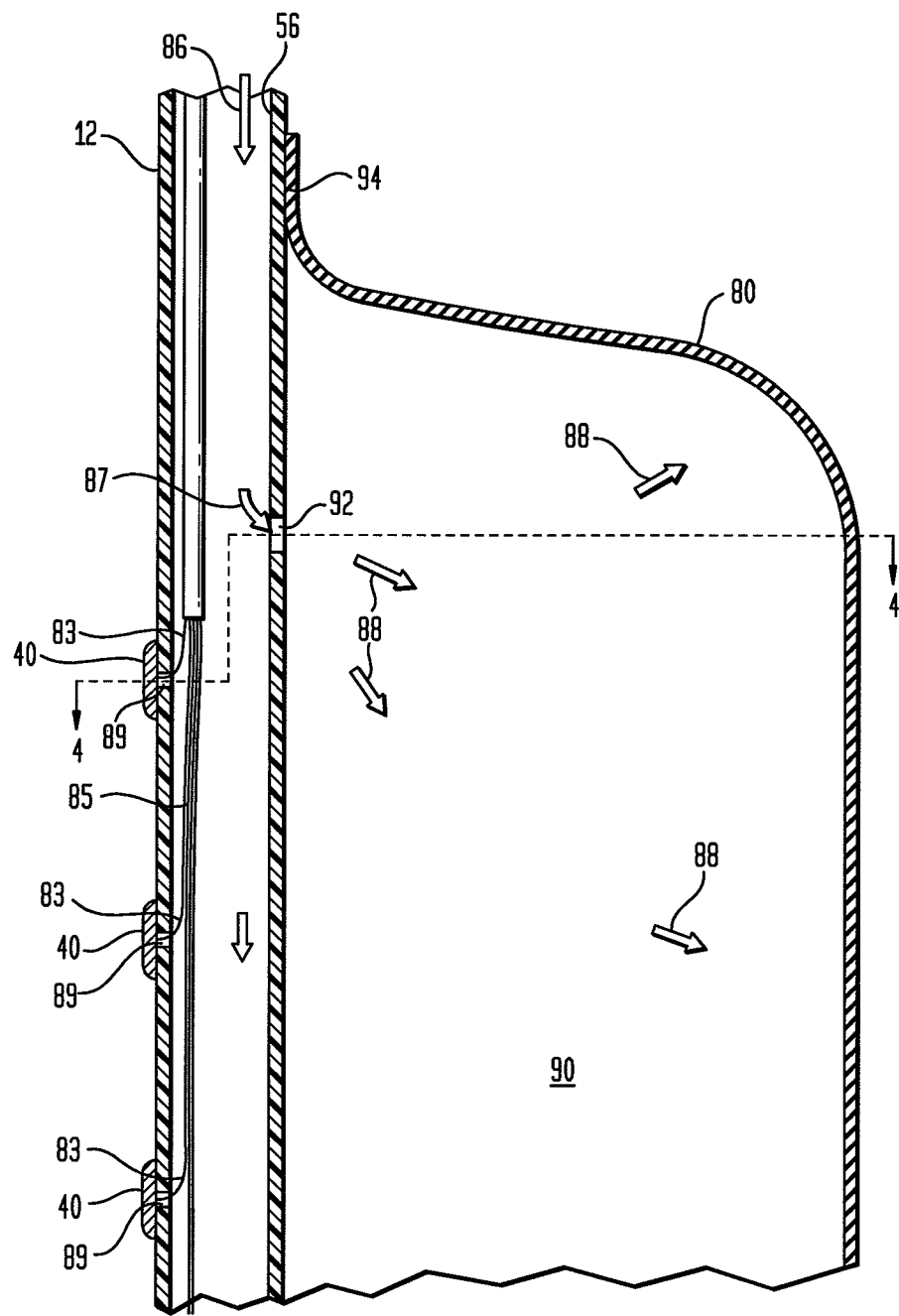
FIG. 3 is an enlarged vertical cross-section of a portion of the catheter of FIG. 1 illustrating an example structure and displacing balloon or bladder inflation method.
Figure 4:
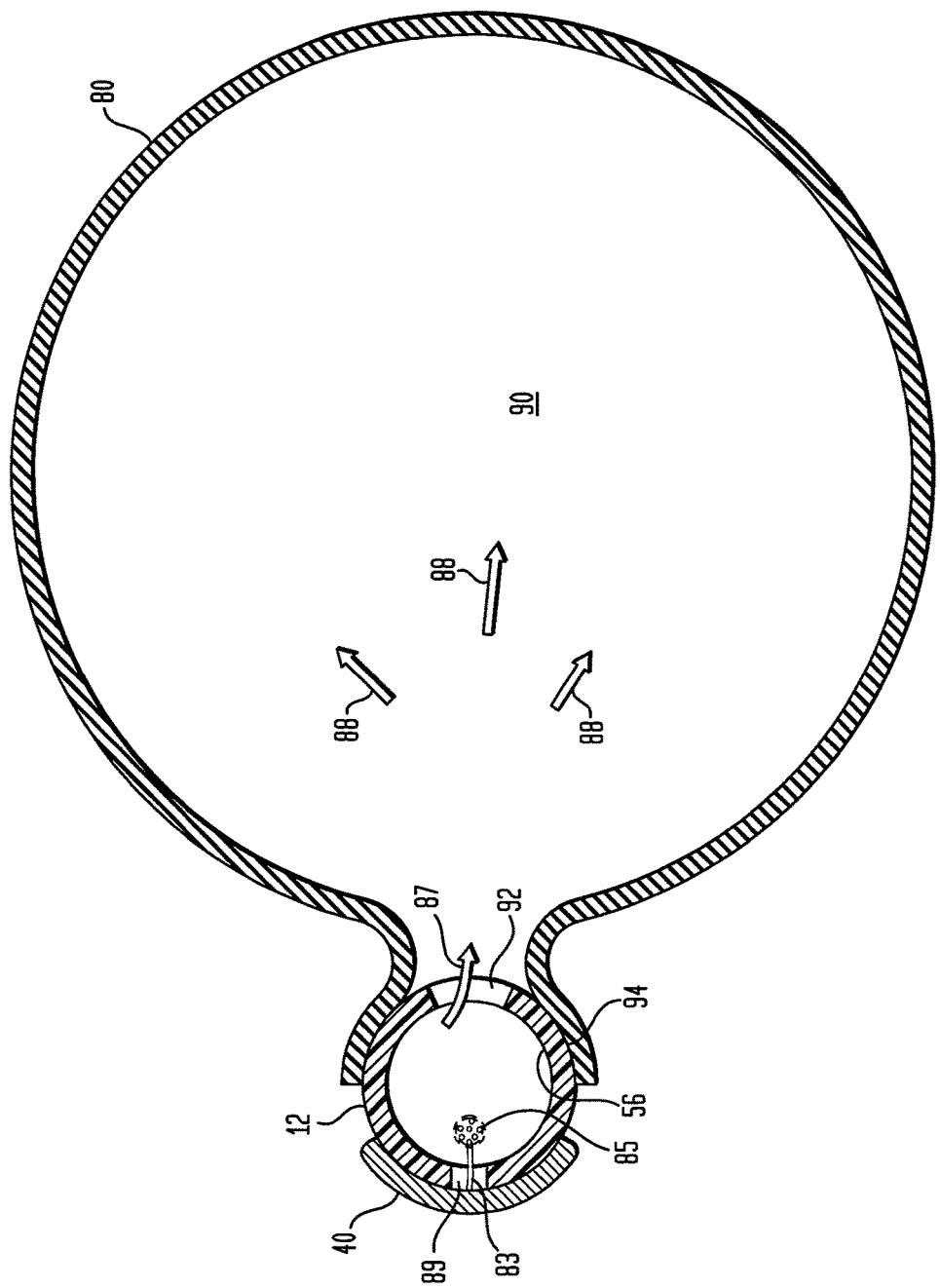
FIG. 4 is an enlarged horizontal cross-section of the catheter of FIG. 1 with the balloon or bladder inflated as taken along the section line 4-4 in FIG. 3.

The balloon or bladder 80 can be inflated by pressurized air or other fluid, which can be directed, for example, through the lumen 56 of the tube 12 into the interior space 90 of the balloon or bladder 80, as illustrated by fluid flow arrows 86, 87, 88 in FIGS. 3 and 4. The balloon or bladder 80 comprises a flexible bag designed to be inflated with air or other gas or liquid, causing it to expand and fill a space that it otherwise does not fill when deflated and collapsed. Either of the terms balloon or bladder is appropriate for this purpose, and those terms may be used interchangeably herein to describe such a component or structure. Therefore, for convenience, this description will proceed with the term balloon, but without any intent to limit the scope of that term vis-a-vis bladder.

One or more holes 92 in the wall of the tube 12 can be provided to allow the air or other inflating fluid to flow from the lumen 56 of the tube 12 into the balloon 80 to inflate the balloon 80 and then to flow back out of the balloon 80 to deflate the balloon 80. The balloon 80 can be attached to the exterior surface of the tube 12 in any convenient, leak-proof manner, for example, with an adhesive 94, or the tube 12 and balloon 80 can be constructed from or with a single manufactured component. The balloon 80 can be made of a stretchable, resilient material or of a non-compliant material, such as Mylar™ or any other minimally conductive or non-conductive material, preferably one that will not leak the inflation fluid into the esophagus E. If the balloon 80 material is non-stretchable, then it can be sized so that, when it is inflated, it expands only to the extent necessary to push the tube 12 and electrodes 40 against the interior wall 84 of the esophagus E, as explained above, regardless of the pressure of the fluid (within re~son so that it does not burst). Enough material to allow expansion of the balloon 80 to a diameter in a range of about 2-3 cm, i.e., the diameter of a typical esophagus E lumen, is generally sufficient. On the other hand, if the material of the balloon 80 is resiliently stretchable, then the pressure of the inflating fluid should be carefully controlled so as to not expand the balloon 80 too much, e.g., not more than the typical 2-3 cm diameter of the esophagus E lumen, in order prevent injury to the esophagus E.

The balloon 80 can be built in a manner such that it extends radially outward from a sector of the tube 12, as illustrated in FIG. 4, for example, a sector in the range of about 45-180 degrees, although this range is not critical. Also, while not shown, there can be more than one balloon 80 mounted on the tube 12 to inflate and extend radially outward from the tube 12. For example, two balloons 80 (not shown) could be mounted side-by-side on the tube 12 so that, together, they could extend from 120 degrees and 270 degrees in relation to the impedance sensor electrodes 40 or at any other angular orientations that effectively push the tube 12 and sensor electrodes 40 against the interior wall 84 of the esophagus E. There can also be more than one balloon 80, mounted at different longitudinal positions along the length of the tube 12 instead of just one balloon.

Each electrode 40 of the example catheter embodiment 10 can be a partial band of electrically conductive material adhered or otherwise attached to the exterior surface of the catheter tube 12, as best seen in FIGS. 3 and 4, although other shapes, for example, buttons or beads, could also be used. Insulated wires 83 in a bundle 85 can be used to connect each electrode independently to the impedance signal generating and processing circuit 106 (FIG. 1) through holes 87 in the tube 12. The bands of electrodes 40 can extend any convenient amount around periphery of the tube 12, for example, but not for limitation, in a range of 30 to 180 degrees. The goal of electrode shape and sizing is to achieve good, direct contact between the electrodes and the mucosa while minimizing or eliminating direct contact between the electrodes and other matter, e.g., bolus remnants, air, liquid, or other artifacts.

Figure 2:
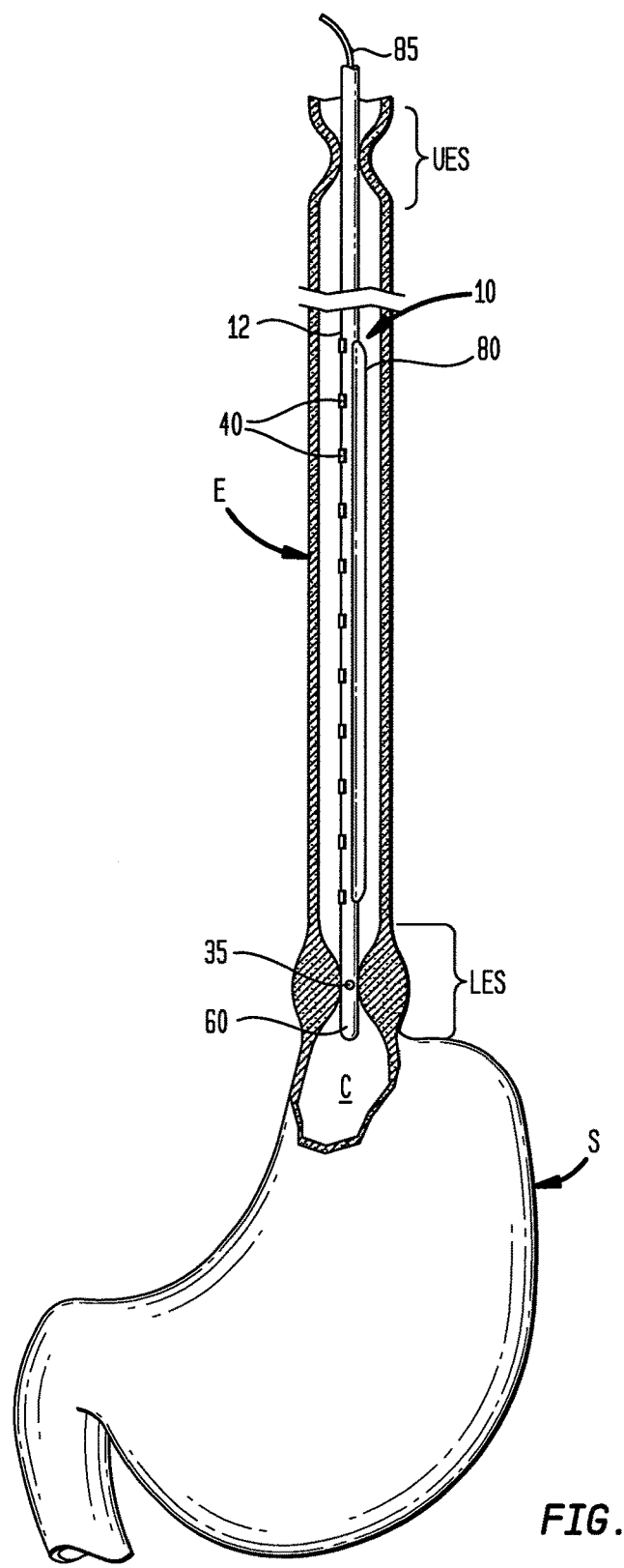
FIG. 2 is a diagrammatic illustration of the catheter of FIG. 1 in the esophagus with the balloon or bladder deflated and collapsed for insertion into, or removal from, the esophagus.

In use, the catheter 10 is inserted through the person's nose or mouth, throat, and upper esophageal sphincter (UES) and into the esophagus E with the balloon 80 deflated, as illustrated in FIG. 2, for ease of insertion and to prevent injury. For impedance recording, mapping, diagnostic, or other purposes, it may be desirable to know the locations of the impedance sensor electrodes 40 in the esophagus E when the impedance of the mucosa is being measured so that the locations where impedance measurements of respective channels 48 can be determined for recording, mapping, diagnostic, and other purposes. For example, but not for limitation, the impedance sensor electrodes 40 can be mounted one centimeter apart from adjacent electrodes 40, as shown in FIG. 1, and the distal-most electrode 40 can be located about one-half of a centimeter above the top of the LES, as also shown in FIG. 1. With eleven of such electrodes 40 spaced 1.0 centimeter apart, this arrangement can provide ten impedance channels 48 evenly spaced over a ten (10) centimeter length of the esophagus E. Each impedance channel 48 measures the impedance of the mucosa between two selected adjacent electrodes 40. Three of the most distal impedance channels 48 are specifically identified in FIG. 1, and, in that example spacing, those three distal impedance channels 48 are considered to be centered at 1.0 cm, 2.0 cm, and 3.0 cm above the top of the LES, respectively. The remaining, more proximal, impedance channels spanning other pairs of electrodes 40 above the distal impedance channels 48 are not specifically identified with part numbers in FIG. 1, to avoid clutter in the drawing, but they are addressable electronically for measurement recording, mapping, etc. Of course, more or fewer electrodes 40, thus impedance channels 48 can be provided, and the distance between electrodes 40 can be different, depending on the desires of a particular clinician or catheter manufacturer. Therefore, impedances measured with the electrodes 40 can be related to specific locations, e.g., levels, of the esophagus E in relation to the LES.

In FIGS. 1 and 2, an optional pressure sensor 35 is shown at or near the distal end 60 of the catheter tube 12 for use in positioning the catheter 10 at a known spatial relationship to the lower esophageal sphincter (LES), where the pressure is normally greater than in the esophagus E above the LES or in the interior cavity C of the stomach S below the LES. The pressure sensed by the optional pressure sensor 35 can be monitored for the greatest pressure as the distal end 60 of the catheter 10 is pushed through the LES and into the stomach S, whereupon the sensed pressure will fall as the pressure sensor 35 enters the internal cavity C of the stomach S. Then, the catheter 10 can be pulled upwardly again until that same greatest pressure is observed from the pressure sensor 35, which indicates that the pressure sensor 35 is located in the LES. Several repetitions of this procedure can be used to ensure the desired position is attained.

Another option without having or using the optional pressure sensor 35 is to sense the greater pressure of the LES on the distal end 60 of the catheter tube 12 caused by the LES with an air or fluid pressure sensor or gauge to sense the pressure in the catheter tube 12. For example, the pressure sensor 212 in the air or inflating fluid supply tube 208 shown in FIG. 6, which is connected in fluid-flow relation to the catheter tube 12, can be used to sense the location of the distal end 60 of the catheter tube 12 in the LES as the distal end 60 is pushed and pulled through the LES. Other positioning or locating devices or methods can also be used.

When the catheter 10 is positioned in the esophagus E as desired, the balloon 80 is inflated with pressurized fluid through the lumen 56 of the tube 12, as explained above, to force the tube 12 and impedance sensor electrodes 40 into direct contact with the inside wall 84 of the esophagus E. In that position, the impedance of the mucosa on the inside wall 84 can be measured, as explained above. After the impedance measurements are completed, the pressure in the tube 12 is released to atmosphere or a negative pressure (vacuum) can be applied to deflate the balloon 80 before pulling the catheter 10 out of the esophagus E. In one embodiment, the balloon 80 could also be evacuated with a vacuum pump, a reversible pressure pump, or other device to ensure it is completely collapsed, as explained below, before pulling the catheter 10 out of the esophagus E. Such evacuation may be particularly beneficial in embodiments that do not use a resilient, stretchable material for the balloon 80.

As explained above, exposure of the esophageal mucosa to acid, e.g., gastric acid and digestive enzymes from the stomach S or duodenum (not shown), for abnormal times or at abnormal levels, typically results in tissue damage, which is manifested in varying degrees of mucosal damage. Milder damage levels are not detectable with routine visual endoscopic examination, while more advanced damage is endoscopically visible as varying degrees of esophagitis or Barrett's esophagus. Exposure of the esophageal mucosa to acid for more than approximately 4.2% of the time poses a significant risk of mucosal damage. Mucosal damage may take the form of microscopic mucosal defects, which are sometimes called "dilated intracellular spaces" or "DIS" for short. Such dilated intracellular spaces provide greater access of luminal refluxate $H^+$ ions to nociceptors within the esophageal mucosa, thereby serving as a basis for enhanced chemoreceptor perception of refluxate, thus pain. The esophageal epithelium of a healthy esophagus provides a structural barrier, which resists the diffusion of refluxed and ingested materials through the mucosa. Abnormal exposure of the esophageal epithelium to reflux of acid, pepsin, and bile from the stomach or duodenum can result in damage to the cellular junction complex of the esophageal epithelium.

The increased salt and water flow allowed by these compromised cellular junctions result in further damage and the eventual development of dilated intracellular spaces in the epithelium. Dilated intracellular space is a recognized morphologic feature in both Gastroesophageal Reflux Disease (GERD) and Non-Erosive Reflux Disease (NERD) patients. Non-Erosive Reflux Disease patients are patients with abnormal esophageal acid exposure, but who still have visually normal esophageal mucosa, as determined by routine endoscopic examination. While not visually recognizable with routine endoscopy, dilated intracellular spaces are an effective early marker of epithelium damage secondary to reflux disease.

In patients with dilated intracellular spaces, the potential difference changes of esophageal tissue with acid perfusion reflect elevated ion permeability of the mucosa. The example mucosal impedance probe 10 with the inflatable balloon 80 for pushing the impedance sensor electrodes 40 into direct contact with the interior wall 84 of the esophagus E, as described above, enables a direct measurement and sensitive assessment of mucosal (epithelial) impedance. By virtue of direct contact of an impedance electrode 40 with the esophageal mucosa, highly accurate determinations of impedance can be made, thereby providing a basis for identification of patients with compromised esophageal mucosa without the need for biopsy and electron microscopy, which was not possible with conventional Multichannel Intraluminal Impedance (MII) reflux monitoring studies for reflux activity detection, because such conventional MII measured values are highly variable and nonspecific to detection of mucosal conditions. Such variability and non-specificity of conventional MII testing is due to differences in conductivity of any air, liquid, or conductive material in the esophagus lumen, and the apparatus and methods of this invention minimize or eliminate such variability and non-specificity, as explained above.

Figure 5:
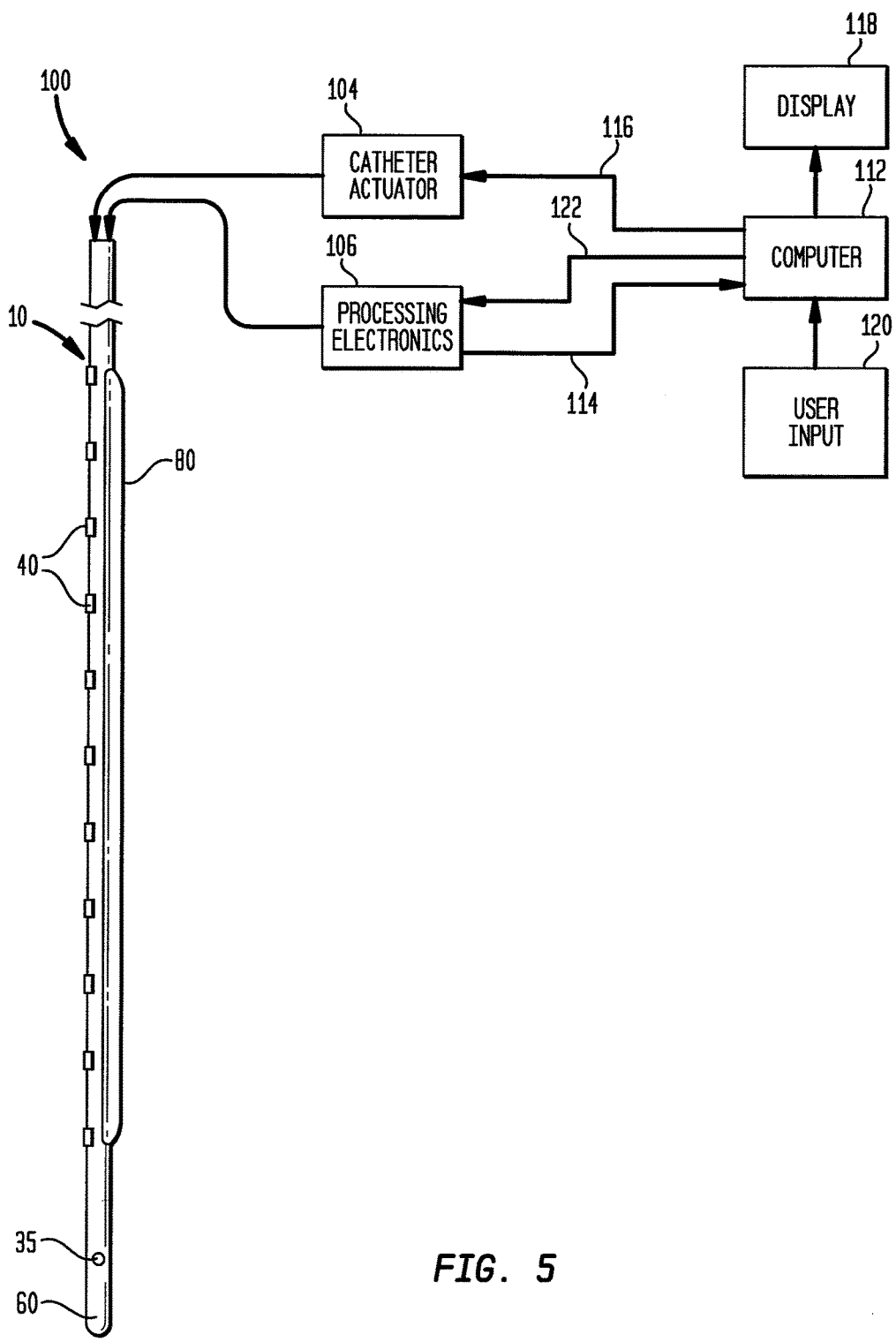
FIG. 5 is a function block diagram of an example embodiment of a mucosal impedance measuring system.

An example embodiment of a mucosa impedance measuring system 100 for implementing mucosa impedance measuring with a mucosa impedance catheter, such as the example mucosal impedance catheter 10 described above, is illustrated in the function block diagram of FIG. 5. Other catheter types or structures can also be used, as explained below, with this example system 100. This example mucosal impedance measuring system 100 includes a catheter, for example the catheter 10 described above, for being positioned in a patient's esophagus in a manner to measure esophageal mucosal impedance at numerous longitudinally spaced locations of the esophageal mucosa, for example, but not for limitation, at one centimeter spacing as described above (FIG. 1). As also explained above, the example catheter 10 includes a balloon 80 that is designed to expand, e.g., by inflation, once placed in the esophageal lumen, so that the impedance sensors 40 on the peripheral surface of the catheter 10 are placed in direct contact with the esophageal mucosa. In this manner, impedance measurements can be made that measure the impedance of the esophageal mucosa between the selected ones of the impedance sensors 40. A catheter activator 104 in FIG. 5 controls the inflation and deflation, thus expansion and contraction, of the balloon 80. The activation and inflation of the balloon 80 on catheter 10 is a controlled process. Enough pressure has to be applied so that the impedance sensors 40 contact the esophageal mucosa with sufficient force to obtain accurate impedance readings, but without creating an excessive deployment pressure, which could damage the patient's esophagus E. Also, excessive pressure on the tissue can cause the impedance of the tissue to change, so controlled pressure is also desirable to minimize or avoid contact pressure based impedance value variations.

As also illustrated in FIG. 5, processing electronics 106 create sensor signals 110 to the electrodes 40 and obtain the impedance measurements resulting from such signals 110, as explained above. Other sensor data may also be acquired, such as pressure sensor data from one or more pressure sensors and data from other sensors that may be disposed in the catheter 10 (e.g., optional pressure sensor 35) or in connecting portions to catheter 10 (e.g., pressure sensor 212 in FIG. 6). The processing electronics 106 creates sensor impedance data 114 and any other data that is applied to computer 112. The computer 112 further processes the data and generates display data in any of a variety of displays, e.g., graphical, maps, numbers, images, sounds, and other known data display formats, any or all of which are represented generically in FIG. 5 by the display function 118.

The computer 112 also generates a control signal 122 that controls the processing electronics 106. For example, computer 112 may generate control signals to perform various different types of impedance measurements, e.g., at different locations or channels or with different voltage or current levels, and could repeat or re-try various measurements. Computer 112 also generates control signal 116 that controls the catheter activator 104. For example, computer 112 may provide an activation control signal 116 to the catheter activator 104 to inflate or deflate the balloon 80 of the catheter 10. In addition, control signal 116 may control the pressure in a pneumatic type of catheter 10, which may be adjusted during various impedance measurements, as detected by computer 112, to obtain additional sensor data. The computer 112 can be any form of computer, microprocessor, or other device or devices programmed to perform the functions described herein, as would be understood by persons skilled in the art. A user input function or device 120 can be connected to computer 112 to enable a user to input commands, data, and other information and to control computer 112. Catheter activator 104 may also include override safety devices that do not allow the balloon 80 to be inflated beyond a certain amount, or to create a pressure greater than a predetermined pressure within the balloon 80.

Figure 6:
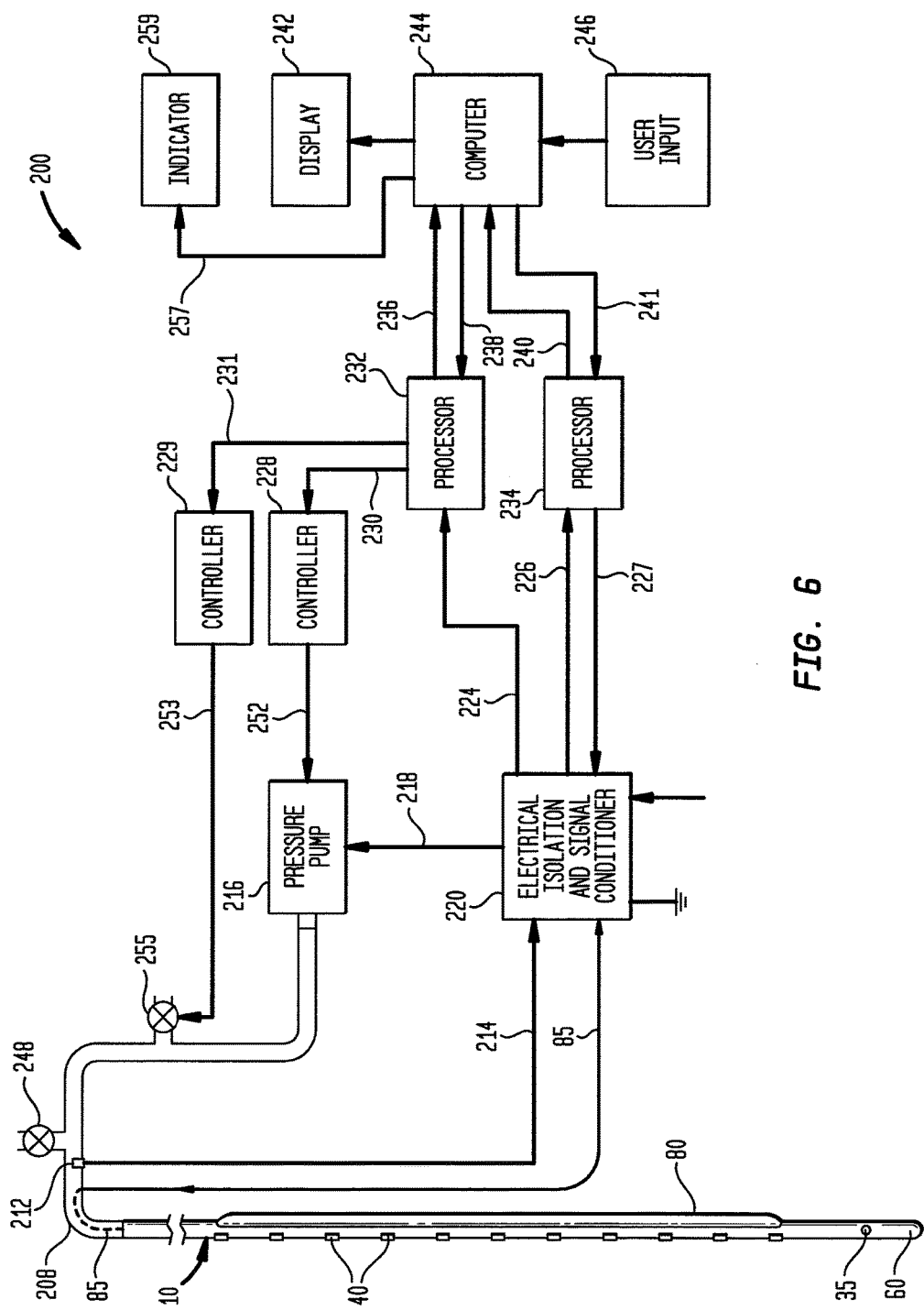
FIG. 6 is a more detailed function block diagram of another example embodiment of a mucosal impedance measuring system.

FIG. 6 is a more detailed block diagram of an example embodiment of a mucosal impedance measuring system 200. As illustrated in FIG. 6, the example catheter 10 is shown with the balloon 80 inflated as it would be after it is inserted into and esophagus E (not shown in FIG. 6) and ready for taking mucosa impedance measurements with the electrodes 40, as described above. Again, other catheter embodiments can also be used with this system, another example of which is described in more detail below. As indicated above, any desired method can be used for inflating the balloon 80. Even a simple syringe assembly (not shown) could be connected to the tube 12 (FIGS. 1-4) or to the tubing 208 in FIG. 6 to push air into the balloon 80 to inflate it and could be pressure controlled by a relief valve preset to the upper limit of a safe inflation pressure. The syringe plunger assembly can be moved in a reverse direction to remove air or fluid from the system to control balloon deflation prior to extubation. The tubing 208, which houses the wires 85 as well as conducts the air or other fluid under pressure to the balloon 80, may comprise surgical tubing that is connected to a pump 216 for pumping air or other fluid into the balloon 80. A pressure relief valve 248 comprises a safety relief valve that ensures that the pressure in tubing 208 and in the balloon 80 does not exceed a predetermined maximum level, which may cause damage to the patient's esophagus or adversely influence impedance readings. In addition, a pressure sensor 212 is disposed in, or connected in fluid-flow relation to, the tubing 208 to measure the air pressure in tubing 208, so that the pump 216 can be controlled and not over inflate the balloon 80. The pressure sensor 212 can also be used to monitor pressure for positioning the catheter 10 in a desired location in the esophagus, as described above. Plurality of wires 83 (FIGS. 3 and 4) in the bundle 85 are connected to the plurality of impedance sensor electrodes 40, as also described below.

As also illustrated in FIG. 6, an electrical isolation and signal conditioner circuit 220 provides electrical isolation for the pressure sensor wires 214, impedance sensor wires 85 and the AC power 218 that is applied to the air pump 216. AC power 222 is applied to the isolation and signal conditioner 220, which generates the isolated AC power signal 218 that is used to run the pump 216. Electrical isolation and signal conditioner 220 may contain signal conditioning circuits that adjust the signal properties of the impedance sensor signals on impedance sensor wires 85, as well as other sensor signals. The adjusted sensor signals 226 are then applied to processor 234. Adjusted pressure signals 224 are applied to processor 232, which processes the pressure signals 224 and generates pressure data 236 that is applied to the computer 244. Pressure control signals 238 are generated by computer 244 and applied to processor 232 which generates control signal 230 in response to the pressure control signals 238. In response to the control signal 230, the controller 228 generates a pressure pump control signal 252 to control the pressure pump 216 to inflate the balloon 80 for the purposes described above. Alternatively, the tubing 208 could simply be connected to a pressurized air or other pressurized fluid system (not shown), in which case a regulator valve (not shown) could be used to turn on and off pressurized fluid flow to the balloon, as would be understood by persons skilled in the art, once they understand this invention.

The signals 238 from the computer 244 also include signals processed by the processor 232 to generate control signals 231 to a controller 229, which generates control signals 253 to a discharge valve 255 to open and close the discharge valve 255. Opening the discharge valve 255 releases the air or other fluid pressure in the tubing 208 and deflates the balloon 80. The computer 244 can use the pressure data 214 from the pressure sensor 212 to monitor and control the pump 216 and the discharge valve 255 to inflate the balloon 80 to a pre-set appropriate pressure and maintain it there during impedance measuring operations and to deflate the balloon 80 when the impedance measuring operations are completed.

If desired, especially, but not necessarily only, when a non-resilient, non-compliant, and minimally conductive or non-conductive balloon 80 material, for example Mylar™ or polyolefin, is used, the pump 216 can be reversible and used to evacuate air or other fluid from balloon 80 to be sure it is fully deflated and collapsed before attempting to pull the catheter 10 out of the esophagus E. The processor 232 can respond to signals from the computer 244 to generate the control signal 231 to the pump controller 228 to generate a pump control signal 265 to reverse the pump 216 to evacuate the balloon 80.

The computer 244 also uses the pressure data 214 to output a signal 257 to an indicator 259 to notify the user whether the balloon 80 is fully deflated, thus safe for insertion into, or extraction from, the esophagus as well as to notify the user when the balloon is inflated to the proper pressure for the impedance measuring operations. Such notification can be visual, audible, or any other convenient notification. Processor 234 processes the isolated sensor signals 226 and generates sensor data 240 that is applied to computer 244. The sensor data is further processed by the computer 244 and displayed on display 242. The display 242 is generic and can include any or all of visual, audible, graphic, paper, electronic, or other types of displays known in the art. The indicator 259 could be combined with the display 242, if desired.

Computer 244 may also generate control signals 241 that are applied to processor 234. Processor 234 processes the control signal 241 and generates signals 227 that are applied to the impedance electrodes 40 via wires 85 to measure the impedance of the esophageal mucosa, for example, but not for limitation, by measuring current flow at a constant voltage, or vice versa, applied to the electrodes 40. Such measuring functions can be performed by the computer 244 or by the processor 234 for any other component (not shown) that can be provided with that capability as would be understood by persons skilled in the art, once they understand this invention.

A user input device for function 246 is also provided for a user to provide various inputs to the computer 244 to operate the system 200, change parameters, override automatic functions, choose and manipulate various displays, input patient data, and the like. Of course, persons skilled in the art will understand that the various functions of the computer and several processors can be combined or separated into one or more devices, microprocessors, computers, and the like, all of which are still within the scope of this inventions as described and claimed.

Figure 7:
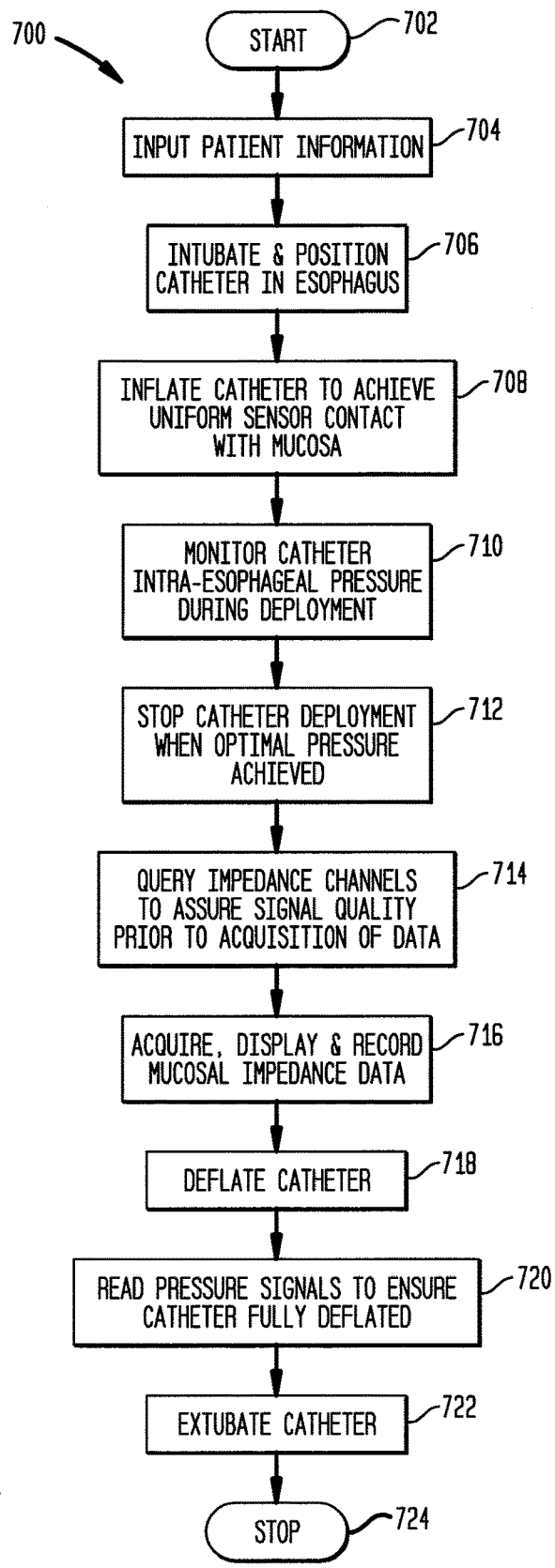
FIG. 7 is a work diagram of one example embodiment of a mucosal impedance measuring system.

FIG. 7 is a work diagram illustrating an example of steps that can be performed with the example catheter 10 and mucosa impedance measuring system 200 described above to obtain impedance measurements of esophageal mucosa using the concepts illustrated by those and other embodiments of this invention. As illustrated in FIG. 7, this example process starts at step 702. At step 704, input information regarding the patient is entered by a user through a user input device, such as input user device 120 (FIG. 5) or user input device 246 (FIG. 6). At step 706, the catheter 10 is intubated and positioned within the esophagus E (for example as illustrated in FIG. 2). This step can include monitoring the intra-esophageal pressure on the catheter 10 during insertion or intubation to determine when the catheter 10 is in a desired position or location in the esophagus E as described above. At step 708, the balloon 80 is inflated to achieve direct electrode 40 contact with the esophageal mucosa on the interior wall 84 of the esophagus E (for example as illustrated in FIG. 1). At step 710, the system (for example, 100 in FIG. 5 or 200 in FIG. 6) monitors the balloon 80 pressure to determine when balloon 80 has been inflated the desired or predetermined amount to position the electrodes 40 in optimal direct contact with optimal pressure against the esophageal mucosa. At step 712, the balloon 80 inflation is stopped when the optimal balloon pressure is achieved, indicating that the catheter 10 is fully and properly deployed in the esophagus E. At step 714, the system 100 or 200 selects and queries the impedance channels by sending impedance signals (e.g., voltage or current) to the selected electrodes 40 (e.g., selected pairs of adjacent electrodes 40) to assure signal quality prior to acquisition of data. In addition, these test signals can provide an indication as to whether the catheter 10 is correctly deployed in the esophagus E or if adjustments need to be made to either the pressure or position of the catheter 10. At step 716, mucosal impedance data is acquired, displayed, and recorded by the mucosal impedance measuring system, for example, the mucosal impedance measuring system 100 (FIG. 5) or the mucosal impedance measuring system 200 (FIG. 6). After the data has been acquired, the balloon 80 of the catheter 10 is deflated and collapsed at step 718. At step 720, the pressure signals from a pressure sensor, such as pressure sensor 212, are read to ensure that the balloon 80 of the catheter 10 is fully deflated. Once it is determined that the balloon 80 is fully deflated, the catheter 10 is extubated at step 722. At step 724, the process is stopped.

Figure 8:
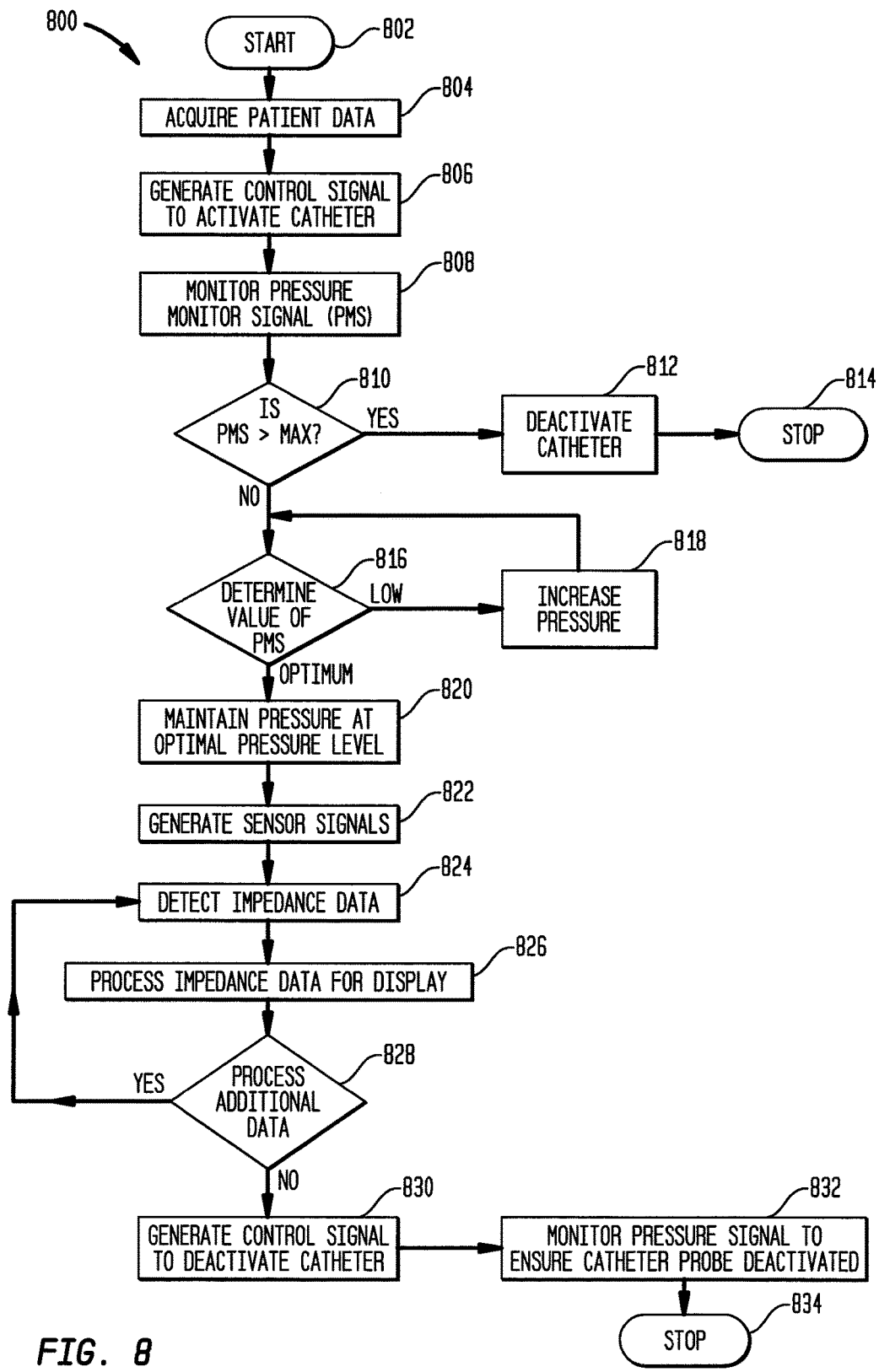
FIG. 8 is a software flow diagram of one example embodiment of a mucosal impedance measuring system.

FIG. 8 illustrates and example software flow diagram 800 of one example embodiment of software that can be utilized in accordance with the present invention. As disclosed in FIG. 8, the process starts at step 802. At step 804, the patient data is acquired. At step 806, control signals are generated to activate the catheter. At step 808, the pressure monitor signal (PMS) is monitored. At step 810, it is determined if the pressure monitor signal (for example the signal 214 from pressure sensor 212 in FIG. 6) indicates a pressure that is greater than a predetermined maximum pressure. If the pressure monitor signal indicates a pressure that reaches that maximum level, the catheter is deactivated at step 812 and the process is stopped at step 814, prior to any damage occurring to the patient. If the pressure monitor signal has not reached a maximum level, at step 816 the value of the pressure monitor signal is determined. If the value of the pressure monitor signal is low, the pressure is increased at step 818 and the process of determining the pressure level, at step 816, is continued. Once the pressure reaches an optimal level, the process proceeds to step 820. At step 820, the pressure is maintained at the optimal pressure level. This optimal pressure level may be achieved by continuously monitoring and adjusting the pressure level through control signals that control an air pump (e.g., the pump 216 in FIG. 6). At step 822, signals are generated to detect the impedance of the esophageal mucosa. As indicated above, test signals may first be generated to determine if the proper pressure and adequate contact between the impedance sensor electrodes 40 and the esophageal mucosa exists. Adjustments may be made prior to reading the impedance data. At step 824, the impedance data is detected. At step 826, the impedance data is processed for display. At step 828, it is determined whether additional data should be collected and processed. If so, the process returns to step 824. If not, the process proceeds to step 830. At step 830, a control signal is generated to deactivate and deflate the catheter 10. The process then proceeds to step 832. At step 832, the pressure signal is monitored to ensure that the catheter probe is deflated for extraction from the esophagus. The process is stopped at step 834.

Figure 9:
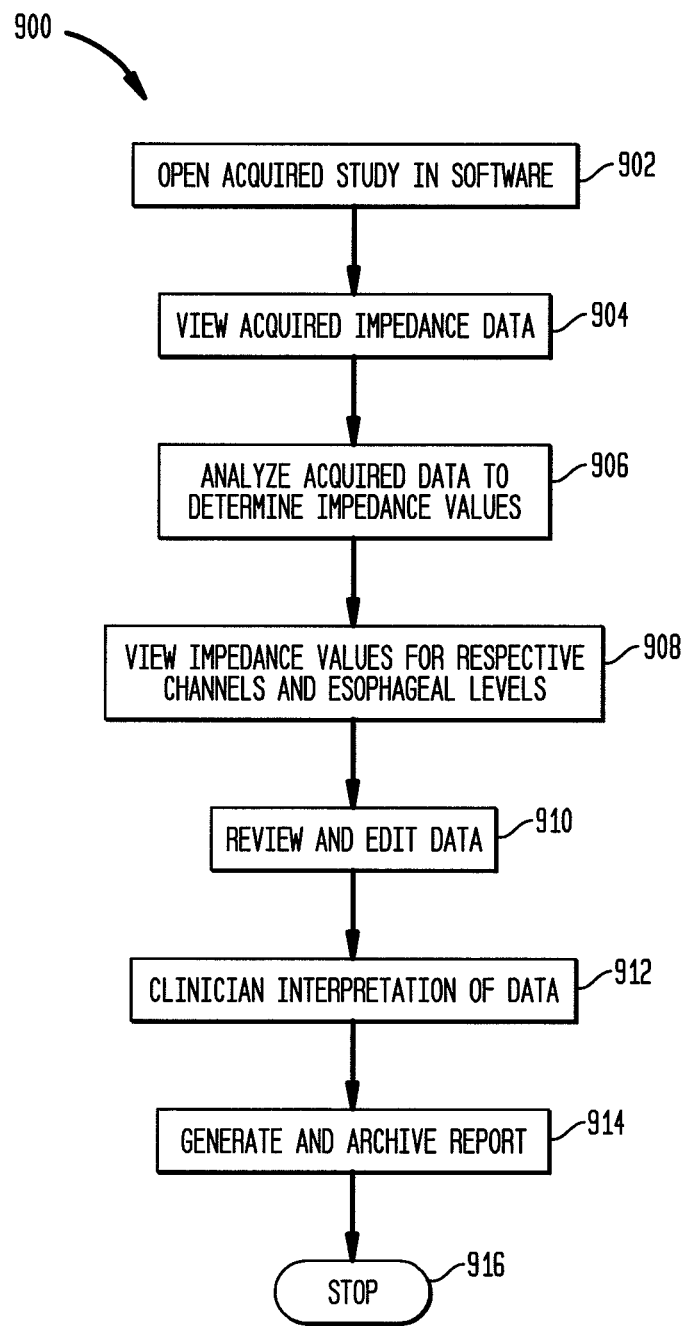
FIG. 9 is an example analysis work flow diagram of one example embodiment of a mucosal impedance measuring system.

FIG. 9 is a work flow diagram 900 illustrating the manner in which the data can be analyzed. At step 902, the collected data for a particular patient is opened for study. At step 904, the acquired impedance data is viewed on a display, such as display 118 (FIG. 5) and display 242 (FIG. 6). At step 906, the acquired data is analyzed to determine impedance values. In a simplified version, the data can be displayed as one or more impedance values, or as a waveform at step 908. More complex analyses can also be performed which may include other parameters such as intraballoon pressure, and mucosal impedance relationships. For example, the acquired impedance data can be opened and then marked, deleted, or edited at step 910 in accordance with time periods when the mucosal impedance is measured. The mucosal impedance data can then be analyzed to measure baseline impedance for each respective channel and mean and median baseline impedance at each respective level of the esophagus. A display of the mucosal impedance baseline differences can be graphically illustrated at the respective levels of the esophagus. In addition, plots can be generated that can illustrate the data in two dimensions or three dimensions, including, but not limited to, bar graphs, line graphs, contour plots, iso-contour plots, etc., and they can be represented in colors for various values or features. The plots may include a graphical representation of the esophageal anatomy. The plot can show the impedance as a function of its physical position in the esophagus. Reports can be generated in textual form or graphical form. The reports can be printed or simply saved in a database or as electronic media. Normal values can be shown and abnormal results can be emphasized by highlighting, color change, font change, etc. Referring again to FIG. 9, the data can then be provided to a clinician for analysis at step 912. At step 914, an archive report can be generated and stored. At step 916, the process is stopped.

Figure 10:
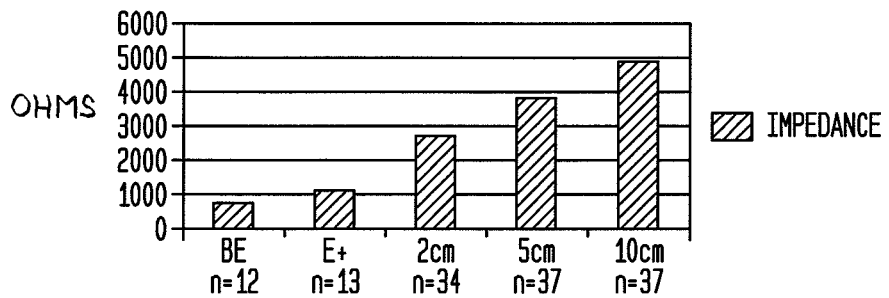
FIG. 10 is a chart of mean mucosal impedance values (in Ohms) for patients at visually perceptible esophagitis and Barrett's esophagus as compared to visually normal esophageal mucosa.

As mentioned above, damaged esophageal mucosa is more conductive of electric current than healthy, undamaged esophageal mucosa. A proof of concept study was conducted using a simplified version of the catheter in FIG. 1 with a single impedance channel comprising two adjacent impedance electrodes. The catheter including the two impedance electrodes was manually pressed to the esophageal mucosa after passage through the working channel of an endoscope. An initial mucosal impedance measurement was taken in each test subject at a distal location in the esophagus by reading the single mucosal impedance channel at the first distal location and then sequentially pulling the catheter upwardly specific distances to reposition the two impedance electrodes at successively more proximal locations and taking impedance measurements at each of the successively more proximal locations. The catheter was connected to a commercially available impedance detection and recording system manufactured by Sandhill Scientific, Inc. Using visual guidance, the mucosal catheter was directly applied to the esophageal mucosa at two centimeters, five centimeters, and ten centimeters proximal to the gastroesophageal junction (LES). When endoscopically visible mucosal erosions were present, mucosal impedance readings were also taken at the site of injury and annotated to quantify esophagitis grade and/or Barrett's mucosa. In endoscopically negative patients (i.e., patients with no visual evidence of mucosal erosion), data was acquired via ambulatory acid reflux monitoring to identify patients with abnormal acid exposure. Research data from the 38 patients was analyzed to determine 5-second mean mucosal impedance values at all esophageal test sites on each respective patient. Patient data was analyzed based on mucosal impedance test site, endoscopic erosion categories, and acid exposure categories. The purpose of the study was to determine if there were mucosal impedance differences in patients with endoscopically normal esophageal mucosa versus patients with esophagitis and Barrett's esophagus. The results of the study showed that, of the 38 test subjects, 13 were esophagitis positive, 9 had Barrett's esophagus, and 16 were endoscopically negative. Of the 16 endoscopically normal subjects, 7 underwent ambulatory pH monitoring to quantify acid exposure. Impedance values in visually normal esophageal mucosa at the 2, 5, and 10 centimeter locations had significantly higher impedance than esophagitis (E+) and Barrett's Esophagitis (BE) sites, as shown in FIG. 10, indicating that non-eroded tissue can be differentiated from eroded tissue using mucosal impedance. In patients with visually normal tissue and normal acid exposure, impedance at the 2, 5, and 10 centimeter locations had only small variations, as shown in FIG.

Figure 11:
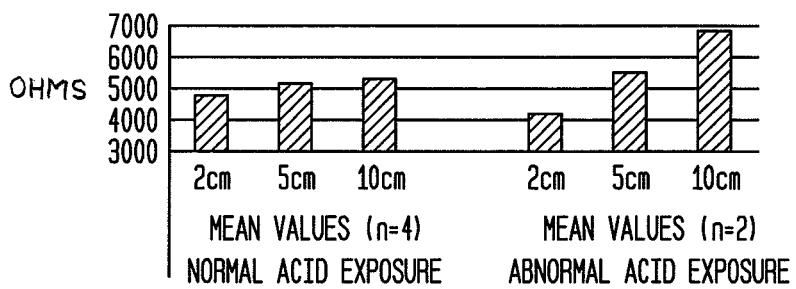
FIG. 11 is a chart showing mucosa impedance values (in Ohms) for patients with visually normal tissue and normal acid exposure and for patients with visually normal tissue and abnormal acid exposure.

11. In patients with visually normal tissue and abnormal acid exposure, commonly referred to as non-erosive reflux disease (NERD), impedance at the 2, 5, and 10 centimeter locations had significant variation with progressively lower impedance moving from proximal to distal sites, as also shown in FIG. 11. Conclusions drawn from this study include the following:

1.) In endoscopically positive patients with visually identifiable damage to the esophageal mucosa, damage is more pronounced in the distal esophageal and progressively less pronounced moving from the distal to proximal esophagus in parallel to the visual observation of mucosal damage suggesting that mucosal impedance measurements could be an alternative marker for GERD. In this patient category, mucosal impedance is 50% to 80% lower in the distal esophagus than in the proximal esophagus validating that mucosal impedance variation in excess of 50% along the length of the esophagus is a marker of pathologic GERD, thus is usable as a difference criteria for GERD.

2) In endoscopically normal patients lacking visually identifiable mucosal damage, two distinct patient categories of mucosal impedance findings are shown:

a.) Visually normal patients with normal acid exposure as measured with ambulatory reflux monitoring have insignificant mucosal impedance variations of less than 20% along the length of the esophagus from distal to proximal. This finding suggests that in patients with less acid reflux (within normal pH parameters) the degree of change in mucosal impedance along the esophagus is less variable than in those with visual mucosal damage or in those with abnormal acid reflux parameters and is usable as a difference criteria for healthy mucosal tissue.

b.) Visually normal patients with abnormal acid exposure as measured with ambulatory reflux monitoring have significant mucosal impedance variations of greater than 40% along the length of the esophagus, thus is usable as a difference criteria for NERD. This finding supports that mucosal impedance measurements may be a sensitive means of defining not only visual damage (GERD) but also chronic acid reflux in those without visual mucosal damage (NERD).

Figure 12:
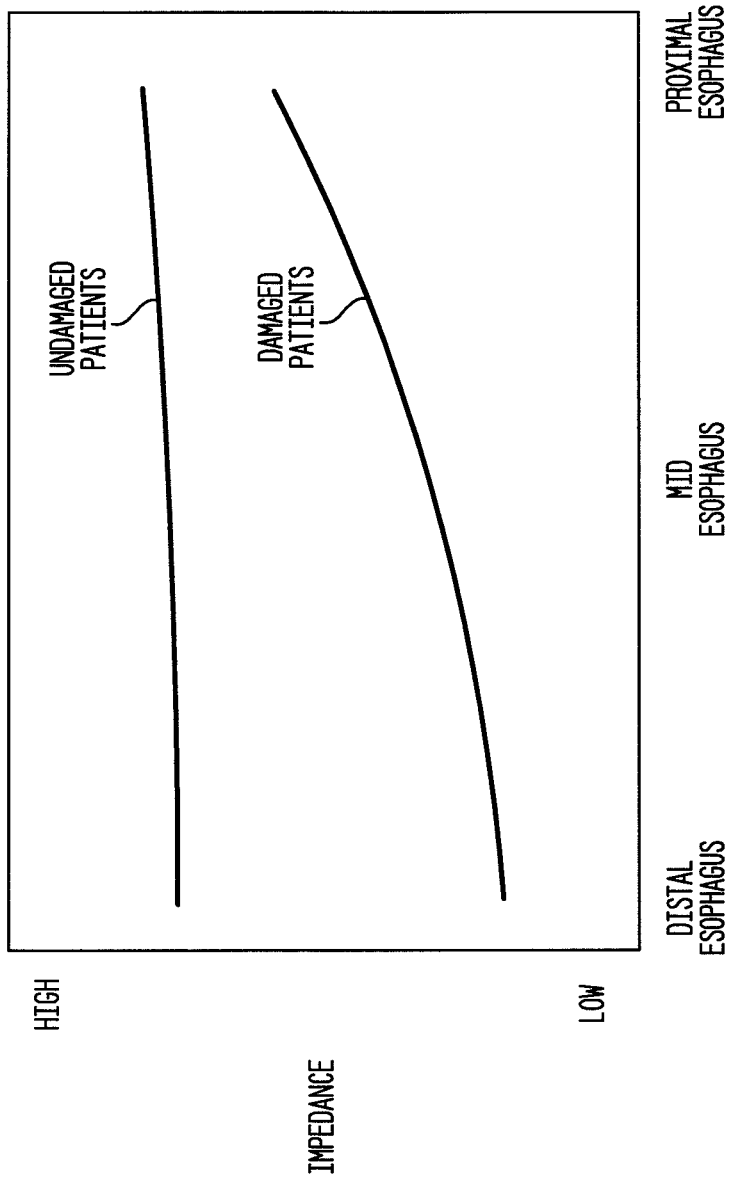
FIG. 12 is a graphical representation of typical impedance value curves for healthy mucosal tissue and diseased or damaged mucosal tissue along the length of the esophagus.

In summary, these results show that mucosal impedance, which is the inverse of mucosal conductivity, is reduced in damaged esophageal mucosa as compared to healthy esophageal mucosa. The data indicate that such impedance reductions are in the range of 50 to 80 percent when esophageal mucosa is damaged, thereby supporting the ability of this invention to make sensitive detections of damaged tissue. Additionally, as illustrated in FIG. 12, mucosal impedance is significantly more variable along the axial length of the esophagus in patients with esophageal damage. In the reflux damaged esophagus, impedance measurements in the distal esophagus (i.e., farther from the mouth and closer to the stomach) are significantly lower than in the proximal esophagus. This distinct variation in mucosal impedance along the axial length of the esophagus may be attributed to progressively greater exposure to damaging reflux fluids from the stomach or duodenum in the distal esophagus versus the proximal esophagus. In undamaged mucosa patients, minimal mucosal impedance changes occur axially along the length of the esophagus as compared to significant changes in reflux damaged patients. These phenomena support the sensitive assessment of mucosal damage both as discreet impedance values and as extent of impedance changes, i.e., impedance differences, between distal and proximal levels along the axial length of the esophagus.

As mentioned above, a more complex analysis involves a relationship between intraballoon pressure and mucosal impedance. More specifically, mucosal impedance changes as the pressure with which the impedance sensors are forced into the mucosa changes, and damaged tissue is more susceptible to impedance changes when the electrodes are pressed into the mucosa surface than healthy tissue. Therefore, the extent to which mucosa impedance changes as a function of pressure applied by the electrodes on the mucosa is also an indicator of tissue damage. In a plot of impedance versus application pressure, normal tissue has a relatively flat plot line, e.g., not much change in impedance as application pressure increases, whereas damaged tissue has a plot line that increases more sharply, i.e., larger changes in impedance as application pressure increases. Application pressure, i.e., the pressure at which the electrodes are pressed against the surface mucosa can be monitored by the pressure in the balloon 80 that pushes the electrodes 40 against the mucosa. Therefore, for example, if more proximal channel 48 impedance measurements remain relatively unchanged or minimal change as pressure in the balloon is increased, while more distal channel 48 impedances decrease more sharply as pressure in the balloon is increased, the indication would be a likelihood of gastroesophageal reflux disease, where, as explained above, more distal portions of the esophagus typically have more mucosal damage than more proximal portions due to more frequent acid reflux exposure. Therefore, differences in impedance changes in different channels 48 located axially higher and lower in the esophagus as a function of balloon 80 pressure changes is indicative of healthy or damaged mucosa. Also, larger impedance changes in distal channels than in proximal channels as a function of changes in applied pressure in the balloon are indicative of gastroesophageal reflux disease.

Figure 13:
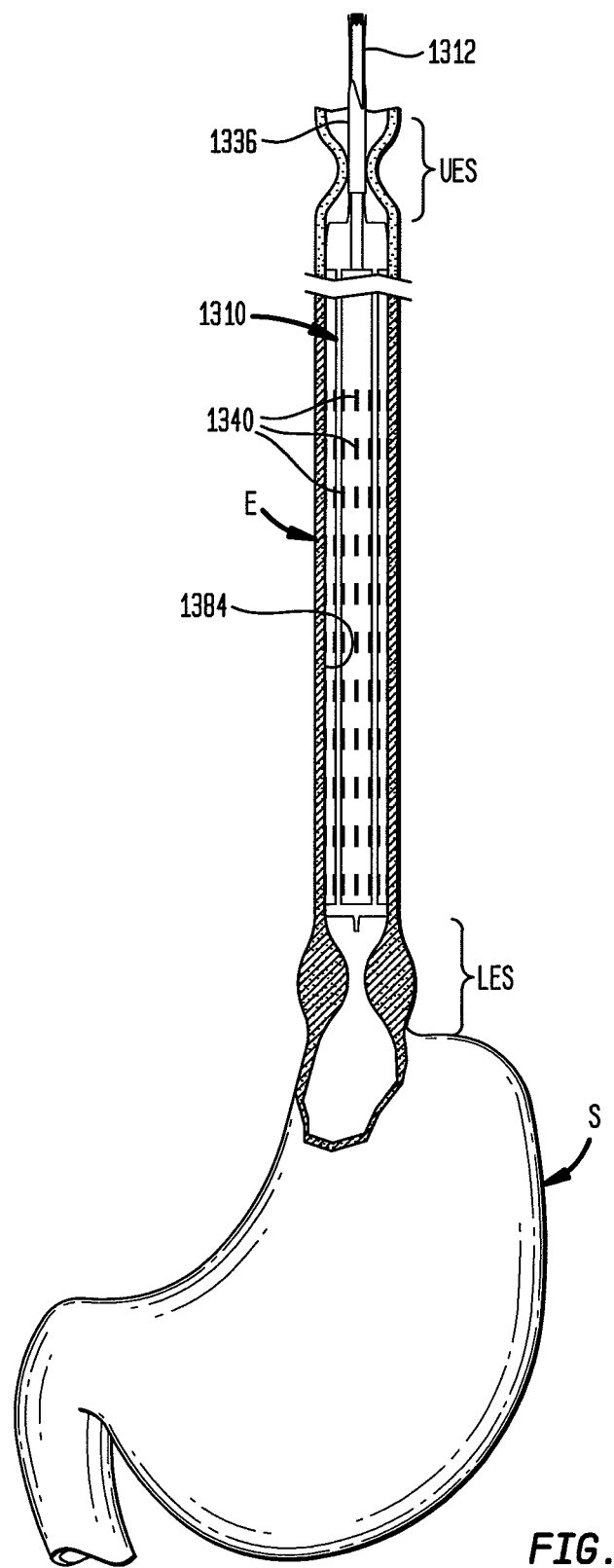
FIG. 13 is a diagrammatic elevation view of another example embodiment of a mucosal impedance catheter with multiple impedance sensor electrodes disposed at divers axial and angular locations on an inflatable balloon or bladder that is inflatable to push the impedance sensor electrodes into contact with multiple, divers axial and angular locations of the mucosal tissue along the length of the esophagus.

Another example embodiment of a mucosal impedance measuring catheter 1310 is illustrated diagrammatically in FIGS. 13-16 for more comprehensive mucosa impedance measuring and mapping. This example catheter 1310 has not just one axial row of impedance sensor electrodes 40 as shown and described above for the example catheter 10 in FIGS. 1-4, but multiple axial rows of electrodes 1340 at a multitude of angular locations about the periphery of the catheter 1310. Therefore, when the catheter 1310 is positioned in the esophagus E and inflated to press the multiple axial and angularly dispersed electrodes 1340 against the mucosa on the interior wall 1384 of the esophagus E, as illustrated in FIG. 13, the electrodes 1340 contact multiple locations of the mucosa at divers locations longitudinally up and down and angularly around the inside wall 1384 of the esophagus E. As such, the impedance of the mucosa can be measured between any selected pair of the electrodes 1340 in the same manner as described above for measuring the impedance between any pair of the electrodes 40 of the catheter 10 in FIGS. 1-4. While not necessary, there are advantages to making each impedance channel to measure impedance between pairs of adjacent electrodes 1340, for example, for accurate impedance measurements at concise locations for usefulness in analyzing and mapping the mucosa for healthy versus damaged epithelial tissue.

Figure 14:
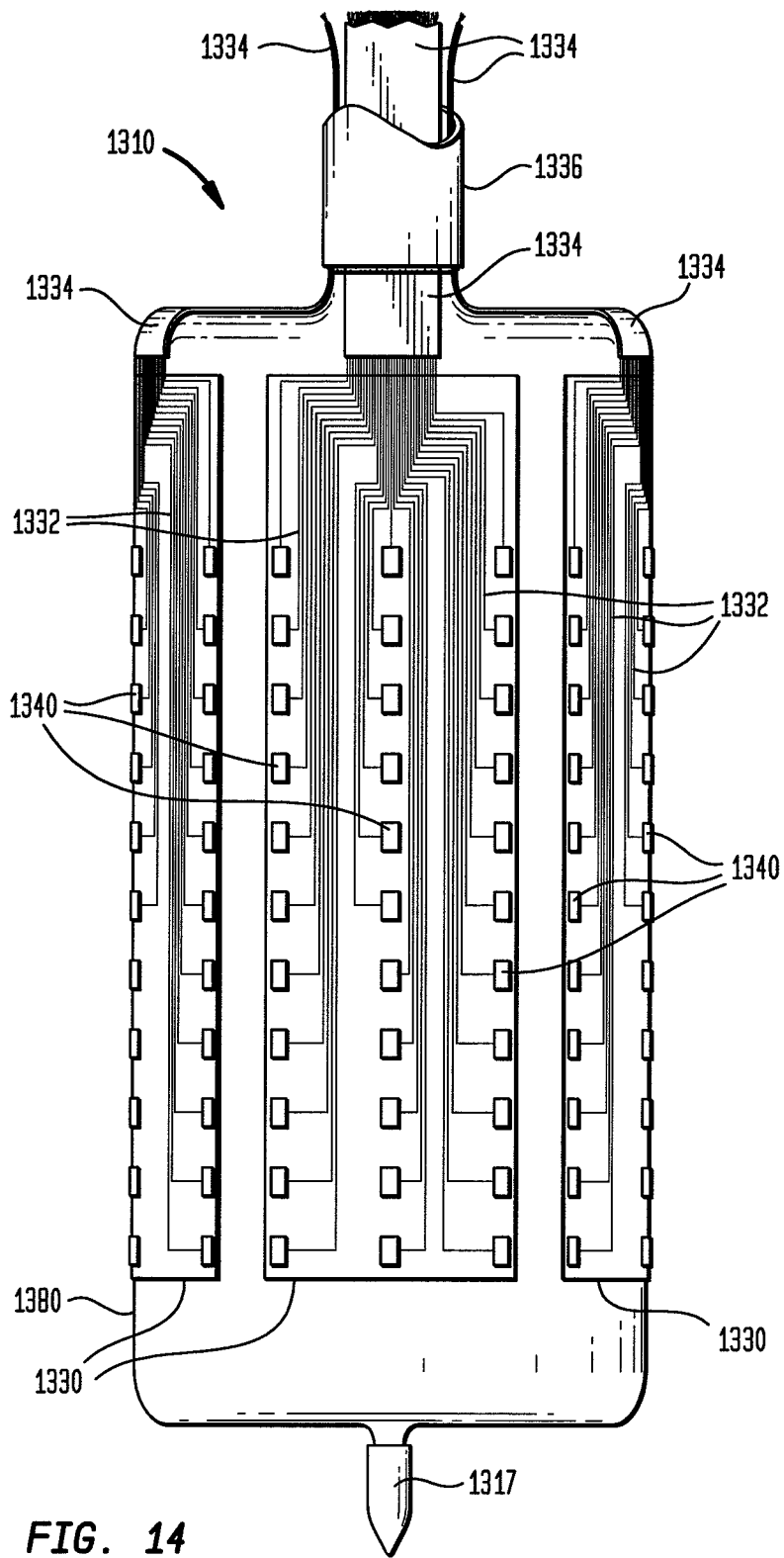
FIG. 14 is an enlarged diagrammatic elevation view of the example mucosal impedance catheter of FIG. 13 illustrating an example structure with flexible integrated circuit boards comprising the impedance sensor electrodes mounted on the peripheral surface of the inflatable balloon or bladder.
Figure 15:
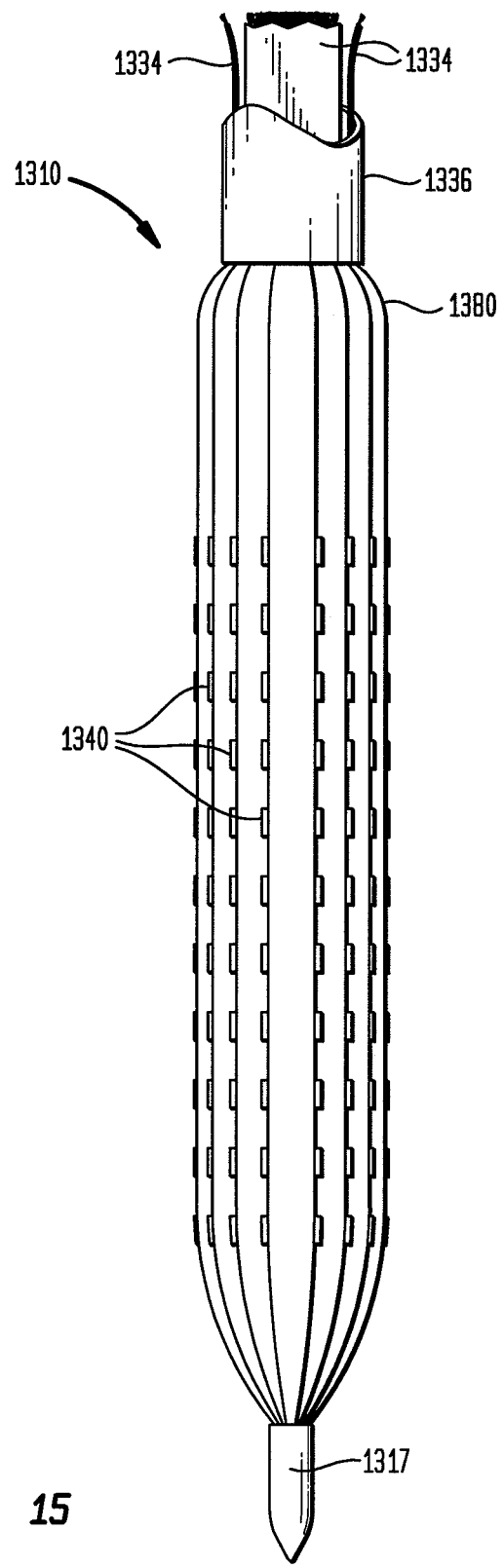
FIG. 15 is an enlarged diagrammatic elevation view of the example mucosal impedance catheter of FIG. 13 deflated and collapsed for insertion into, or extraction from, the esophagus.
Figure 16:
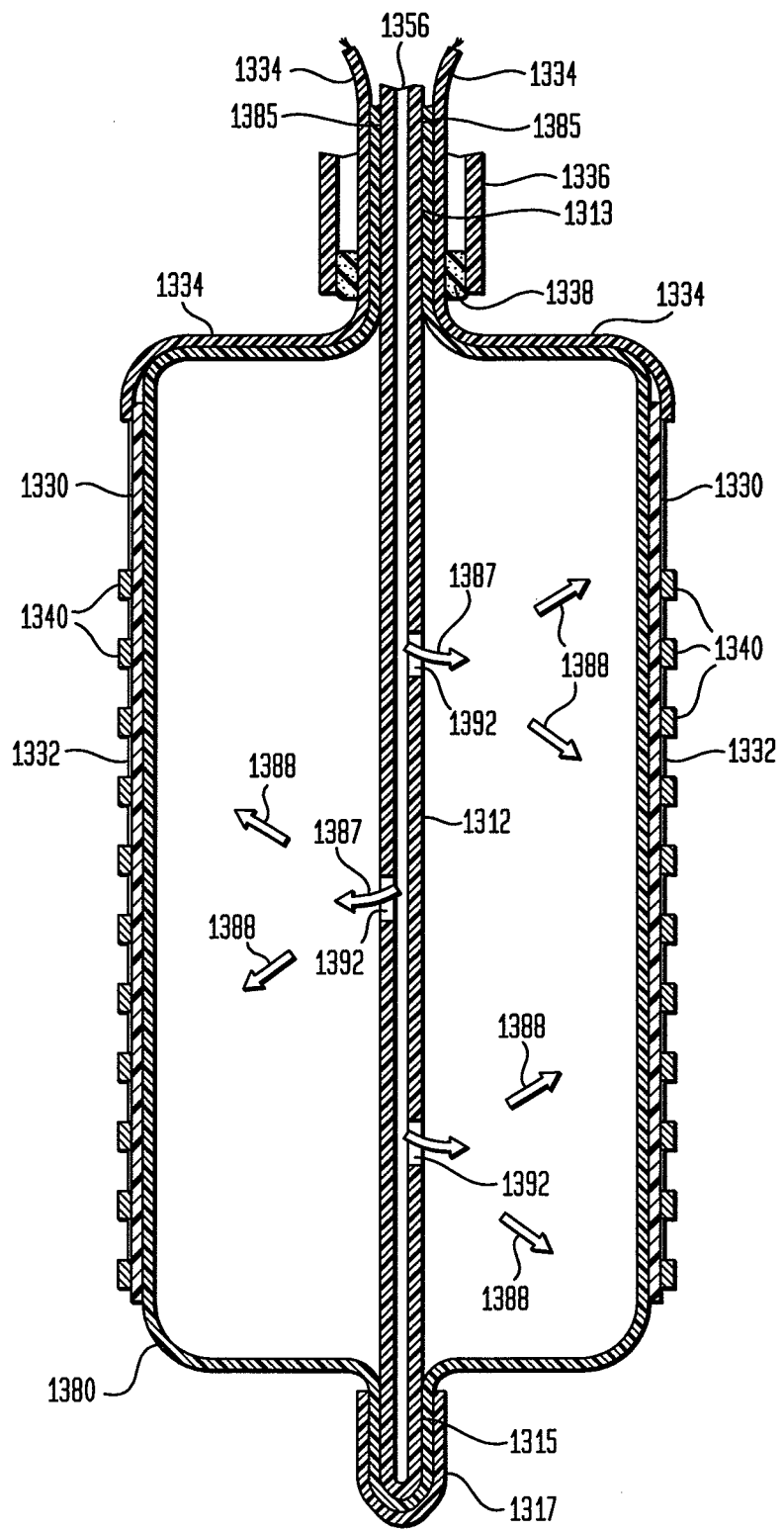
FIG. 16 is an enlarged diagrammatic view in longitudinal cross-section of the mucosal impedance catheter of FIG. 13 to illustrate an example inflatable structure and inflation method.
Figure 17:
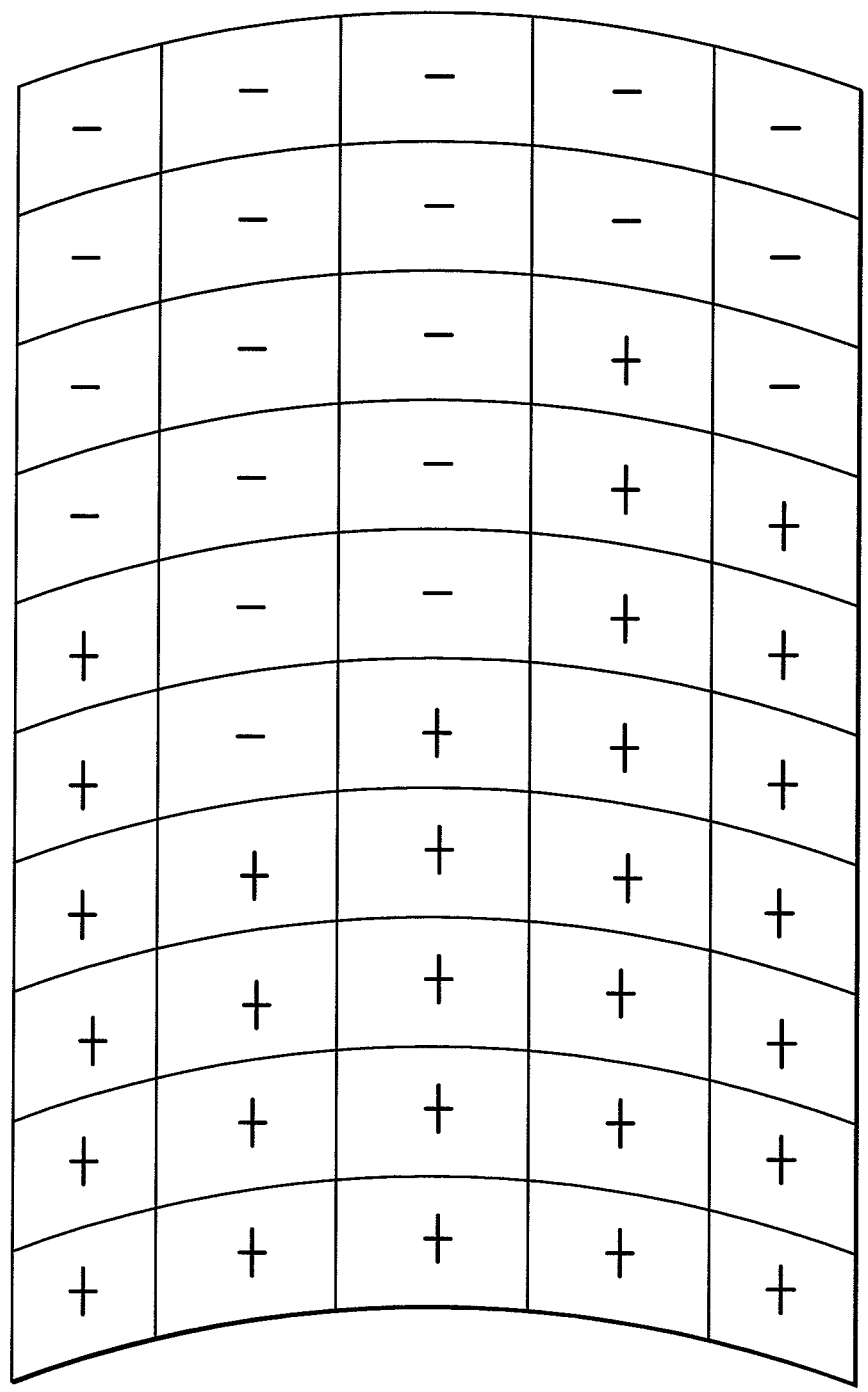
FIG. 17 is a diagrammatic view of an example esophageal mucosa mapping display illustrating areas of healthy and damaged mucosa utilizing mucosal impedance data obtained from an esophagus with the multiple axially and angularly disposed impedance sensor electrodes of the example mucosal impedance catheter of FIGS. 13-16.

Referring now primarily to FIGS. 14 and 16, the catheter 1310 comprises a thin, flexible, balloon 1380 mounted around a length of a thin, inner tube 1312, as best seen in FIG. 16. The inner tube 1312 is stiff enough to be pushed into an esophagus E, carrying along with it the thin, flexible balloon 1380 when the balloon 1380 is deflated and collapsed, as shown in FIG. 15, but soft and flexible enough to minimize likelihood of injury to the esophagus as the catheter 1310 is being pushed into the esophagus during intubation. The inner tube 1312 also has one or more holes 1392 through its wall inside the balloon 1380 so that pressurized air or other inflating fluid pumped into the lumen 1356 of the inner tube 1312 is directed into the balloon 1380, as indicated by the flow arrows 1387, 1388 in FIG. 16, to inflate and expand the balloon 1380 in the esophagus E as shown in FIG. 13 to press the electrodes 1340 on the peripheral surface of the catheter 1310 into direct contact with the mucosa for acquiring the esophageal mucosa impedance measurements. The inflation air or other fluid can also be released or evacuated from the balloon 1380 through those holes 1392 to deflate and collapse the balloon 1380, as illustrated in FIG. 14, before the catheter 1310 is pulled out of the esophagus E. The balloon 1380 material can be adhered or otherwise fastened in a leak-proof manner to the inner tube 1312, as indicated at 1313 and 1315 in FIG. 16. A flexible, resilient, distal end cap 1317 can be mounted on the distal end of the tube 1312, as shown in FIG. 16, to help seal the balloon 1380 to the distal end of the inner tube 1312 or to seal the distal end of the inner tube 1312, as best seen in FIG. 16, as well as to help guide the tube 1312 into and through the esophagus during intubation.

The mucosal impedance sensor electrodes 1340 can be fastened to divers locations axially up and down and angularly around the exterior surface of the balloon 1380 in any convenient manner. The thin, flexible, printed circuit boards 1330, each comprising multiple impedance sensor electrodes 1340, shown in FIGS. 14, 16, is one example electrode 1340 mounting structure that mounts the electrodes 1340 at divers locations longitudinally up and down and angularly around the balloon 1380. The thin, flexible, printed circuit boards 1330 can be made of any thin, flexible, electrically non-conductive material, for example, Mylar™ or polyolefin, that conforms with the inflated expansion and deflated collapsed conditions of the balloon 1380. The thin, flexible, printed circuit boards 1330 can include electric traces 1332 to connect the individual electrodes 1340 on the printed circuit boards 1330 to impedance signal generating and acquisition systems, for example, but not for limitation, those shown in FIGS. 5 and 6 and described above. Any number of printed circuit boards 1330 can be used, or the balloon 1380 itself can be made as a unitary printed circuit board.

The catheter 1310 has all of the functionalities described above in relation to the in-line electrode catheter 10 and systems 100 and 200 described above, but with more electrodes 1340 and electrode pair channels available, especially dispersed both longitudinally and angularly around the periphery of the balloon 1380. The electric traces 1332 of the printed circuit boards 1330 can be connected to the impedance signal generating and acquisition systems, e.g., 100, 200, in any convenient manner, for example, but not for limitation, via the ribbon wires 1334 shown in FIGS. 14 and 16 comprising multiple strands of individual wires or conductors. As another example, elongated extensions (not shown) of the thin, flexible, printed circuit boards 1330 themselves could contain the traces extended all the way to the signal generating and processing systems (e.g., 100, 200) outside the patient's body and generally outside the catheter 1310. As also shown in FIGS. 14 and 16, the inner tube 1312 and ribbon wires 1334 (or substitute elongated extensions of the printed circuit board) are housed in an outer catheter tube or sleeve 1336, which is long enough to extend from the balloon 1380 in the esophagus E to the outside of the patient's body. The upper or proximal end portions 1385 of the balloon 1380 can also be gathered and secured into the proximal end of the outer catheter tube 1336 for neatness and additional fastening of the balloon 1380 to the inner tube 1312, and then a sealer 1338 can be applied or injected into the distal end of the outer tube or sleeve 1336, as shown in FIG. 16.

As mentioned above, the mucosal impedance catheter 1310 with its electrodes 1340 dispersed longitudinally and angularly on the surface of the balloon 1380 of the catheter 1310 provides a number of additional data sources, impedance measurements, and mapping points of a patient's esophagus for determining existence, location, and extent of damage in the esophagus. For example, a representation of various impedances from numerous test locations in a patient's esophagus can be viewed in three-dimension graphical images (not shown) or unwrapped for better visibility of the results, as illustrated in FIG. 15. For example, the X (vertical) coordinate or edges can represent the distance from the lower esophageal sphincter (LES) at which a particular impedance value was obtained or some other reference point, and the Y (horizontal) coordinate or edges can represent the distance around the circumference of the esophagus, relative to some reference point. Scalar values (e.g., "+" or "−") of the impedance data can then be plotted on the two dimensional chart, for example as shown on the chart in FIG. 15. Shading or colors (not shown) can also provide a visual representation of the scalar values with any number of shades, intensities, or variations for any number of scale values.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of detecting and measuring the condition of intraluminal esophageal mucosa, the method comprising:
    (a) intubating an esophagus with a catheter comprising an inflatable and deflatable balloon and at least one impedance sensing electrode on an exterior surface of the catheter;
    (b) inflating the balloon to press the at least one impedance sensing electrode into a mucosa of the interior esophageal wall; and
    (c) directing an electric current through the mucosa via the at least one impedance sensing electrode while the at least one impedance sensing electrode is pressed by the balloon against the mucosa and measuring impedance of the mucosa, using an impedance measuring system including a processor, to indicate the condition of the mucosa wherein the impedance of the mucosa as measured is dependent on a pressure with which the balloon presses the at least one impedance sensing electrode against the mucosa.

2. The method of claim 1, further comprising the step of comparing impedance data obtained during measuring impedance of the mucosa and identifying tissue having tissue characteristics of an esophageal disease based on the impedance data.

3. The method of claim 2, wherein tissue having tissue characteristics of the esophageal disease have lower impedance values than healthy tissue.

4. The method of claim 2, wherein a variation of mucosal impedance between the distal and proximal esophagus is 50% to 80% for patients with the esophageal disease.

5. The method of claim 2, wherein a variation of mucosal impedance between the distal and proximal esophagus is less than 20% for visually normal patients with normal acid exposure and is more than 40% for visually normal patients with abnormal acid exposure.

6. The method of claim 1, wherein step (a) further comprises:
measuring a pressure at the distal end of the catheter to determine a position of a lower esophageal sphincter and thereafter positioning the distal end of the catheter at a known spatial relationship to the lower esophageal sphincter.

7. The method of claim 1, wherein step (a) further comprises:
sensing a pressure at the distal end of the catheter to determine a position of a lower esophageal sphincter by using at least one of an air and a fluid pressure sensor in fluid-flow communication with a tube of the catheter to sense a pressure in the tube.

8. The method of claim 1, wherein step (b) further comprises:
controlling a pressure with which the at least one impedance sensing electrode is pressed into the mucosa of the interior esophageal wall in order to prevent injury to the esophagus and avoid contact pressure based impedance value variations.

9. The method of claim 1, wherein step (c) further comprises:
controlling an application pressure between the at least one impedance sensing electrode and the mucosa of the interior esophageal wall;
measuring changes in impedance of the mucosa as a function of the application pressure; and
comparing changes in impedance of the mucosa as a function of the application pressure to identify a presence of at least one of an esophageal disease.

10. The method of claim 9, wherein greater changes in impedance of the mucosa as a function of application pressure are indicative of the esophageal disease.

11. The method of claim 10, wherein the change of impedance of the mucosa as a function of application pressure for healthy tissue is less than that of damaged tissue.

12. The method of claim 1, wherein the at least one impedance sensing electrode includes a plurality of impedance sensing electrodes.

13. The method of claim 12, wherein the separation between at least two of the plurality of impedance sensing electrodes is less than 1 cm.

14. The method of claim 12, wherein the plurality of impedance sensing electrodes positioned longitudinally and angularly on the external surface of the balloon, wherein the step of inflating the balloon includes pressing the plurality of impedance sensing electrodes into the mucosa of the interior esophageal wall, and wherein the step of directing the electric current through the mucosa includes directing the electric current through the mucosa via the plurality of impedance sensing electrodes while the plurality of impedance sensing electrodes are pressed by the balloon against the mucosa and measuring impedance of the mucosa.

15. The method of claim 14, further comprising mapping the mucosa for healthy versus damaged epithelial tissue in the esophagus using impedance data obtained from measuring the impedance of the mucosa.

16. The method of claim 15, wherein the step of mapping the mucosa tissue includes using impedance data from the plurality of impedance sensing electrodes to produce a multi-dimensional graphic that represents an extent of damage to the esophagus.

17. The method of claim 14, wherein a plurality of flexible conductors are positioned on the inflatable and deflatable balloon.

18. The method of claim 17, wherein the plurality of flexible conductors include electric traces connected to at least some of the plurality of impedance sensing electrodes.

19. The method of claim 1, further comprising the step of deflating the balloon and pulling the catheter out of the esophagus.

20. The method of claim 1, wherein, during step (b), the at least one impedance sensing electrode is pressed into direct contact with the mucosa of the interior esophageal wall.

21. The method of claim 1, wherein the balloon is inflated to a pre-set pressure and maintained at the pre-set pressure during measuring impedance of the mucosa.

22. A method of detecting and measuring the condition of intraluminal esophageal mucosa, the method comprising:
(a) intubating an esophagus with a catheter comprising at least one impedance sensing electrode on an exterior surface of the catheter;
(b) pressing the at least one impedance sensing electrode into a mucosa of the interior esophageal wall; and
(c) directing an electric current through the mucosa via the at least one impedance sensing electrode while the at least one impedance sensing electrode is pressed against the mucosa and measuring impedance of the mucosa, using an impedance measuring system including a processor, to indicate the condition of the mucosa wherein the impedance of the mucosa as measured is dependent on a pressure with which the at least one impedance sensing electrode is pressed against the mucosa.

23. The method of claim 22, wherein at least one impedance sensing electrode is pressed against the mucosa at a pre-set pressure and maintained at the pre-set pressure during measuring impedance of the mucosa.

24. A method of detecting and measuring the condition of intraluminal esophageal mucosa, the method comprising:
(a) intubating an esophagus with a catheter comprising an inflatable and deflatable balloon and at least one impedance sensing electrode on an exterior surface of the catheter;
(b) inflating the balloon to press the at least one impedance sensing electrode into a mucosa of the interior esophageal wall; and
(c) directing an electric current through the mucosa via the at least one impedance sensing electrode while the at least one impedance sensing electrode is pressed by the balloon against the mucosa and measuring impedance of the mucosa, using an impedance measuring system including a processor, to produce a pressure-regulated impedance measurement indicative of the condition of the intraluminal esophageal mucosa.

25. The method of claim 24, wherein the impedance measuring system in electrical communication with the at least one impedance sensing electrode produces the electric current directed through the mucosa and acquires the pressure-regulated impedance measurement.

26. A method of detecting and measuring the condition of intraluminal esophageal mucosa, the method comprising:
(a) intubating an esophagus with a catheter comprising at least one impedance sensing electrode on an exterior surface of the catheter;
(b) pressing the at least one impedance sensing electrode into a mucosa of the interior esophageal wall; and
(c) directing an electric current through the mucosa via the at least one impedance sensing electrode while the at least one impedance sensing electrode is pressed against the mucosa and measuring impedance of the mucosa, using an impedance measuring system including a processor, to produce a pressure-regulated impedance measurement indicative of the condition of the intraluminal esophageal mucosa.

27. The method of claim 26, wherein the impedance measuring system in electrical communication with the at least one impedance sensing electrode produces the electric current directed through the mucosa and acquires the pressure-regulated impedance measurement.

* * * * *